US012594028B1

(12) United States Patent
Etkin et al.

(10) Patent No.: US 12,594,028 B1
(45) Date of Patent: Apr. 7, 2026

(54) EEG MONTAGE FOR FACILITATING SELECTION OF DRUG TREATMENT IN PATIENTS SUFFERING FROM PSYCHIATRIC DISORDERS

(71) Applicant: Alto Neuroscience, Inc., Mountain View, CA (US)

(72) Inventors: Amit Etkin, Mountain View, CA (US); Sarah Long, Mountain View, CA (US); Iliana Bray, Mountain View, CA (US); Akshay Sujatha Ravindran, Mountain View, CA (US)

(73) Assignee: ALTO NEUROSCIENCE, INC., Mountain View, CA (US)

( * ) Notice: Subject to any disclaimer, the term of this patent is extended or adjusted under 35 U.S.C. 154(b) by 0 days.

(21) Appl. No.: 19/047,415

(22) Filed: Feb. 6, 2025

(51) Int. Cl.
| | |
|---|---|
| *A61B 5/00* | (2006.01) |
| *A61B 5/16* | (2006.01) |
| *A61B 5/369* | (2021.01) |
| *A61K 31/165* | (2006.01) |

(52) U.S. Cl.
CPC ............ *A61B 5/4848* (2013.01); *A61B 5/165* (2013.01); *A61B 5/369* (2021.01); *A61K 31/165* (2013.01)

(58) Field of Classification Search
None
See application file for complete search history.

(56) References Cited

U.S. PATENT DOCUMENTS

| | | | | |
|---|---|---|---|---|
| 3,859,988 | A | * | 1/1975 | Lencioni, Jr. .......... A61B 5/276 |
| | | | | 324/500 |
| 3,993,046 | A | * | 11/1976 | Fernandez ............. A61B 5/369 |
| | | | | 600/545 |
| 5,225,442 | A | | 7/1993 | Andrieux et al. |
| 2006/0173510 | A1 | * | 8/2006 | Besio ..................... A61B 5/375 |
| | | | | 607/45 |
| 2014/0221780 | A1 | * | 8/2014 | Goldberger .......... A61B 5/0205 |
| | | | | 600/300 |
| 2015/0157235 | A1 | * | 6/2015 | Jelen ...................... A61B 5/291 |
| | | | | 600/383 |
| 2015/0313498 | A1 | * | 11/2015 | Coleman .................. A61B 5/38 |
| | | | | 600/383 |
| 2018/0256912 | A1 | * | 9/2018 | Leuchter .............. A61B 5/4836 |
| 2021/0353224 | A1 | * | 11/2021 | Etkin ...................... G16H 30/40 |
| 2022/0387424 | A1 | | 12/2022 | Etkin et al. |

FOREIGN PATENT DOCUMENTS

| | | |
|---|---|---|
| EP | 0447285 A1 | 9/1991 |
| WO | 2020081609 A1 | 4/2020 |

OTHER PUBLICATIONS

International Search Report and Written Opinion in PCT/US2024/030416 on Sep. 4, 2024.

(Continued)

*Primary Examiner* — Jason M Sims
*Assistant Examiner* — Matthew Eric Ogles
(74) *Attorney, Agent, or Firm* — Blank Rome LLP

(57) ABSTRACT
This invention relates to the use of a reduced number of electroencephalogram (EEG) channels for predicting those who would benefit from drug treatment (such as with agomelatine) in patients with a psychiatric disorder (such as depression), as well as to an electroencephalogram (EEG) device for recording EEG data at these EEG channels.

8 Claims, 19 Drawing Sheets

(56)                 References Cited

OTHER PUBLICATIONS

Corruble, Emmanuelle , et al., "Efficacy of Agomelatine and Escitalopram on Depression, Subjective sleep and Emotional Experiences in Patients with Major Depressive Disorder: a 24-wk Randomized, Controlled, Double-blind Trial,", International Journal of Neuropsychopharmacology, 2013, 16:2219-2234, XP055729756.

Cukic, Milena , et al., "When Heart Beats Differently in Depression: A Review of HRV Measures,", arxiv.org, Cornell University Library, 201 Olin Library Cornell University Itacha, NY 14853, 2021, pp. 3-5, XP091077614.

Desseilles et al., Journal of Clinical Psychiatry, 2011, 72(8):1152-1154.

Fineberg, N.A. , et al., "P.2.102 Effect of Agomelatine on The Sleep EEP in Patients with Major Depressive Disorder (MMD)", European Neuropsychophamacology, Elsevier Science Publishers BV, Amsterdam, NL, 2015, 15:S435-S436, XP005514625.

Lau, ZJ , et al., "Brain entropy, fractal dimensions and predictability: A review of complexity measures for EEG in healthy and neuropsychiatric populations.", Eur J Neurosci., 2022, 56(7):5047-5069. doi: 10.1111/ejn.15800. Epub Sep. 2, 2022. PMID: 35985344; PMCID: PMC9826422 (Year: 2022).

Norman et al., Expert Opinion on Pharmacotherapy, 20:6, 647-656 (2019).

Pandi-Perumal, Seithikurippu R, et al., "Bidirectional Communication Between Sleep and Circadian Rhythms and Its Implications for Depression: Lessons from Agomelatine,", Progress in Neurobiology, 2009, 88:264-271, XP026337933.

Potmesil, P , "What combinations of agomelatine with other antidepressants could be successful during the treatment of major depressive disorder or anxiety disorders in clinical practice?", Ther Adv Psychopharmacol. Jul. 7, 2019;9-11 (Year: 2019).

Quera-Salva, Maria-Antonia, et al., "Impact of the Novel Antidepressant Agomelatine on Disturbed Sleep-wake Cycles in Depressed Patients", Hum. Psychopharmacol Clin Exp, 2010, 25:222-229, XP071720525.

Saeedi, Physical and Engineering Sciences in Medicine (2020) 43:1007-1018.

Safayari, Medicine in Novel Technology and Devices 12 (2021) 100102. p. 1-16 (Year: 2021).

Skalski, M , et al., "Pharmaco-Electroencephalography-Based Assessment of Antidepressant Drug Efficacy—The Use of Magnesium Ions in the Treatment of Depression.", J Clin Med. Jul. 15, 2021;10(14):3135. (Year: 2021).

Watts, D, et al., "Predicting Treatment Response Using EEG in Major Depressive Disorder: A Machine-learning Meta-Analysis", Transl Psychiatry, 12, 332 (2022).

Wichniak, Adam , et al., "Sleep as a Biomarker for Depression,", International Review of Psychiatry, 2013, 25:5:632-645, XP093131643.

Laux et al., Clin. Pract. 2014, 18(2):86-96.

Salva et al., Int J Neuropsychopharmacology 2007, 10:691-696.

Dubocovich et al., Current Opinion in Investigational Drugs, 2006, 7:7:670-680 XP008078929.

Cukic, Cognitive Neurodynamics, 2020, 14:443-455.

Dahale, General Hospital Psychiatry, 2014, 36:e3, p. 1.

* cited by examiner

EEG MONTAGE FOR FACILITATING SELECTION OF DRUG TREATMENT IN PATIENTS SUFFERING FROM PSYCHIATRIC DISORDERS

FIELD OF THE INVENTION

This invention relates to the use of a reduced number of electroencephalogram (EEG) channels for predicting those who would benefit from drug treatment (such as with agomelatine), as well as to an electroencephalogram (EEG) device for recording EEG data at these EEG channels.

BACKGROUND OF THE INVENTION

Clinical care for depression involves assessment and diagnosis based on a set of clinician-assessed and patient-reported symptoms such as depressed mood, anhedonia, appetite changes, sleep and psychomotor changes but notably no biological or quantitative behavioral variables. When an assessment such as a magnetic resonance imaging (MRI) scan or a blood test is performed, it is to rule out non-psychiatric causes of depression which may necessitate treatments other than an antidepressant medication, including causes such as hypothyroidism, dementia or metabolic disruptions. After diagnosing a patient with depression, a clinician may then prescribe one of multiple antidepressant treatments, which primarily includes drugs such as selective serotonin reuptake inhibitors (SSRIs), serotonin norepinephrine reuptake inhibitors (SNRIs), and norepinephrine dopamine reuptake inhibitors (NDRIs), or atypical antidepressants. Notably, however, selection of antidepressant medication is done purely by trial-and-error, with no biological or quantitative behavioral measures to inform medication choice. Typically, SSRIs are selected as the first line treatment based on their general tolerability, but not because they are known to be more effective for the broader patient population, nor more effective for that particular patient. Most patients, however, fail to respond adequately to the first medication (Trivedi et al., *Am J Psychiatry*, 2006, 163 (1): 28-4, doi: 10.1176/appi.ajp.163.1.2, PMID 16390886), at which point selection of the next medication again follows a trial-and-error process. Indeed, it has been found that on average, failing one SSRI does not necessarily predict a different response to another SSRI versus an SNRI or NDRI (Rush et al., *N Engl J Med.* 2006, 354:1231-1242). Further there is no clear guidance if one should augment an antidepressant with an insufficient response or switch to a different antidepressant since both options have similar outcomes. As such, clinical assessments typical of clinical care interactions do not provide information sufficiently useful for selection of subsequent medication trials, and therefore external information required by the clinician to improve medication selection is not available.

One medication that may differ in its mechanisms and clinical effects from conventional SSRIs/SNRIs is agomelatine (N-[2-(7-methoxynaphthalen-1-yl)ethyl]acetamide) which, unlike other conventional antidepressants, stimulates melatonin receptors and blocks serotonin 5-HT$_{2C}$ receptors.

There is often uncertainty as to which patients are most responsive to agomelatine (i.e., those for whom it would be critical to prescribe a drug with otherwise questionable efficacy across unselected depression patients). This state of uncertainty is further amplified when considering the use of agomelatine as an adjunct to a failed conventional antidepressant, about which little is known clinically. Consequently, SSRIs continue to be the most common medication prescribed in clinical practice, even through multiple rounds of failed medication trials. When deviations are made it is to the use of SNRIs and NDRIs alone or in combination with SSRIs, or addition of an atypical antipsychotic (Wu et al., PLOS One, 2019, 14: e0220763). By contrast, agomelatine is the least-prescribed of conventional antidepressants in markets where it is approved (Forns et al., *J Affect Disord,* 2019, 249:242-252).

Moreover, inasmuch as any measurement is done of patients as part of clinical care, clinicians only have access to patient-reported or clinician-observed clinical signs and symptoms. Thus, clinicians do not have a basis upon which to select any one medication over another and would hence not be able to discern who would best respond to agomelatine. As such, no measures exist for identifying agomelatine-responsive patients prior to treatment. Definition of such signals would have a major impact on the ability to prescribe agomelatine in a manner that best aligns its action with clinical benefits for a defined subpopulation of patients with depression or a comorbid illness.

SUMMARY OF THE INVENTION

It has now been found that the effects of a drug treatment, such as agomelatine treatment, on a patient suffering from a psychiatric disorder, can be predicted by a pattern of brain activity as recorded through electroencephalography (EEG) using a reduced electrode configuration.

One aspect of the present invention is a method of selecting a drug treatment for a patient suffering from a psychiatric disorder (such as depression) that comprises collecting brain wave activity data via one of certain EEG electrode configurations applied to a patient; analyzing the brain wave activity data to predict an outcome of the drug treatment in the patient based on one or more EEG measures; and selecting the patient for drug treatment based on the outcome prediction. The electrode configuration (i) includes no more than 18 electrodes, (ii) comprises four or more electrodes from around the circumference of the head of the patient, and (iii) two or more electrodes from the midline of the head of the patient. In one embodiment, the configuration comprises (i) four or more electrodes selected from Fp1, Fp2, F7, F8, T3, T4, T5, T6, O1, and O2 and (ii) two or more electrodes selected from Fz, Cz, and Pz, according to the 10-20 system of electrode placement. In another embodiment, the configuration comprises (i) four or more electrodes selected from Fp1, Fp2, AF7, AF8, F7, F8, FT7, FT8, T7, T8, TP7, TP8, P7, P8, PO7, PO8, O1, and O2 and (ii) two or more electrodes selected from Fpz, AFz, Fz, FCz, Cz, CPz, Pz, POz, and Oz, according to the 10-10 system of electrode placement. In yet another embodiment, the electrode configuration is (i) a 7-channel electrode configuration consisting of electrodes at F7-Fz-F8-Cz-P7-Pz-P8, (ii) an 8-channel electrode configuration consisting of electrodes at F7-Fz-F8-Cz-P7-Pz-P8-Oz, (iii) an 8-channel electrode configuration consisting of electrodes at F7-Fz-F8-Cz-P7-Pz-P8-Fpz, (iv) an 8-channel electrode configuration consisting of electrodes at F7-Fz-F8-Cz-P7-Pz-P8-AUX, where the auxiliary (AUX) channel is a general electrophysiology channel (e.g., allowing for EEG, electrooculogram (EOG), electromyogram (EMG), or electrocardiogram (EKG) input), or (v) a 6-channel electrode configuration consisting of electrodes at Cz-Pz-Fp1-Fp2-P7-P8, according to the 10-10 system of electrode placement. The electrode configurations described herein are also referred to collectively as "reduced electrode configurations."

In one preferred embodiment, the electrode configuration is a 7-channel electrode configuration consisting of electrodes at F7-Fz-F8-Cz-P7-Pz-P8, according to the 10-10 system of electrode placement.

In another embodiment, the electrode configuration is an 8-channel electrode configuration consisting of electrodes at F7-Fz-F8-Cz-P7-Pz-P8-Oz, according to the 10-10 system of electrode placement.

In another embodiment, the electrode configuration is an 8-channel electrode configuration consisting of electrodes at F7-Fz-F8-Cz-P7-Pz-P8-Fpz, according to the 10-10 system of electrode placement.

In another embodiment, the electrode configuration is an 8-channel electrode configuration consisting of electrodes at F7-Fz-F8-Cz-P7-Pz-P8-AUX, according to the 10-10 system of electrode placement, where the auxiliary (AUX) channel is a general electrophysiology channel.

In yet another embodiment, the electrode configuration is a 6-channel electrode configuration consisting of electrodes at Cz-Pz-Fp1-Fp2-P7-P8, according to the 10-10 system of electrode placement.

In one embodiment, the configuration may include one or two reference electrodes, for example on the earlobe or on the mastoid.

The present invention may further provide a method of selecting an agomelatine treatment in depressed patients that comprises collecting brain wave activity data via an electrode configuration of EEG electrodes applied to a patient; analyzing the brain wave activity data to predict an outcome of the agomelatine treatment in the patient based on one or more EEG measures; and selecting the patient for agomelatine treatment based on the outcome prediction. The electrode configuration (i) includes no more than 18 electrodes, (ii) comprises four or more electrodes from around the circumference of the head of the patient, and (iii) two or more electrodes from the midline of the head of the patient. In one embodiment, the configuration comprises (i) four or more electrodes selected from Fp1, Fp2, F7, F8, T3, T4, T5, T6, O1, and O2 and (ii) two or more electrodes selected from Fz, Cz, and Pz, according to the 10-20 system of electrode placement. In another embodiment, the configuration comprises (i) four or more electrodes selected from Fp1, Fp2, AF7, AF8, F7, F8, FT7, FT8, T7, T8, TP7, TP8, P7, P8, PO7, PO8, O1, and O2 and (ii) two or more electrodes selected from Fpz, AFz, Fz, FCz, Cz, CPz, Pz, POz, and Oz, according to the 10-10 system of electrode placement. In yet another embodiment, the electrode configuration is (i) a 7-channel electrode configuration consisting of electrodes at F7-Fz-F8-Cz-P7-Pz-P8, (ii) an 8-channel electrode configuration consisting of electrodes at F7-Fz-F8-Cz-P7-Pz-P8-Oz, (iii) an 8-channel electrode configuration consisting of electrodes at F7-Fz-F8-Cz-P7-Pz-P8-Fpz, (iv) an 8-channel electrode configuration consisting of electrodes at F7-Fz-F8-Cz-P7-Pz-P8-AUX, where the auxiliary (AUX) channel is a general electrophysiology channel, or (v) a 6-channel electrode configuration consisting of electrodes at Cz-Pz-Fp1-Fp2-P7-P8, according to the 10-10 system of electrode placement.

In certain embodiments, the one or more EEG measures are selected from EEG measures of entropy or complexity, and any combination thereof; the one or more EEG measures is EEG sample entropy at the Pz electrode; the one or more EEG measures are measures of predictability, measures of regularity, or any combination thereof; and/or the one or more EEG measures are selected from approximate entropy, detrended fluctuation analysis, Higuchi fractal dimension, Katz fractal dimension, largest Lyapunov exponent, modified multiscale entropy, multiscale entropy, aperiodic exponent, and any combination thereof.

In an embodiment, the agomelatine treatment comprises administration of agomelatine, a pharmaceutically acceptable salt thereof, or a prodrug thereof.

In other embodiments, the one or more EEG measures are analyzed with stored historical subject data containing data from a plurality of subjects having a depressive disorder, who received treatment with agomelatine, a prodrug thereof, or a pharmaceutically acceptable salt thereof, wherein the stored historical subject data include for a plurality of the subjects, the efficacy of the agomelatine treatment and one or more of the same type of EEG measures as calculated for the patient; and/or the step of analyzing the brain wave activity data to predict an outcome of the agomelatine treatment in the patient comprises determining an agomelatine efficacy likelihood score for the patient based on the stored historical subject data; and selecting the patient based on the likelihood score.

Yet another aspect is a method of treating major depressive disorder or the depressive phase of bipolar disorder in a patient or treating depressive symptoms in a patient having post-traumatic stress disorder (PTSD), where the patient is being treated with one or more antidepressants other than agomelatine (or a prodrug or salt thereof) but has failed to adequately respond to the one or more antidepressants. Where the patient, prior to initiation of agomelatine treatment, exhibits high sample entropy in the low gamma frequency range (30-40 Hz) of their EEG collected with a reduced electrode configuration described herein, the method includes administering a therapeutically effective amount of (a) agomelatine, a prodrug thereof, or a pharmaceutically acceptable salt thereof and (b) the one or more antidepressants. In other words, the agomelatine (or a prodrug thereof or salt thereof) is administered as an adjunctive therapy to one or more currently prescribed antidepressants, where the patient previously failed to respond to the one or more antidepressants. In one embodiment, the EEG measures are taken while the patient is resting, with eyes closed (REC). In one embodiment, the patient suffers from major depressive disorder and PTSD.

Yet another aspect is a method of treating the depressive phase of bipolar disorder in a patient, where the patient is being treated with one or more mood stabilizers and/or one or more antidepressants other than agomelatine (or a prodrug or salt thereof), but has failed to adequately respond to the one or more mood stabilizers and/or antidepressants. Where the patient, prior to initiation of agomelatine treatment, exhibits high sample entropy in the low gamma frequency range (30-40 Hz) of their EEG collected with a reduced electrode configuration described herein, the method includes administering a therapeutically effective amount of (a) agomelatine, a prodrug thereof, or a pharmaceutically acceptable salt thereof and (b) the one or more mood stabilizers and/or one or more antidepressants. In other words, the agomelatine (or a prodrug or salt thereof) is administered as an adjunctive therapy to one or more currently prescribed mood stabilizers and/or antidepressants, where the patient previously failed to respond to the one or more antidepressants. In one embodiment, the EEG measures are taken while the patient is resting, with eyes closed (REC). In one embodiment, the patient suffers from major depressive disorder and PTSD.

Yet another embodiment is a method of treating major depressive disorder or the depressive phase of bipolar disorder in a patient or treating depressive symptoms in a patient having PTSD, where the patient, prior to initiation of treatment with agomelatine (or a prodrug or salt thereof), exhibits high sample entropy in the low gamma frequency range (30-40 Hz) of their EEG collected with a reduced electrode configuration described herein. The method includes administering a therapeutically effective amount of (a) agomelatine, a prodrug thereof, or a pharmaceutically acceptable salt thereof and optionally (b) one or more antidepressants (e.g., one antidepressant) other than ago-melatine (or a prodrug or salt thereof). In one embodiment, the EEG measures are taken while the patient is resting, with eyes closed (REC). In one embodiment, the patient prior to treatment with the combination of agomelatine (or a prodrug or salt thereof) and the one or more antidepressants was not treated with an antidepressant. In one embodiment, the patient suffers from major depressive disorder and PTSD.

Yet another embodiment is a method of treating the depressive phase of bipolar disorder in a patient, where the patient, prior to initiation of treatment with agomelatine (or a prodrug or salt thereof), exhibits high EEG sample entropy using low gamma frequency range (30-40 Hz) electroen-cephalography with a reduced electrode configuration described herein. The method includes administering a therapeutically effective amount of (a) agomelatine, a prod-rug thereof, or a pharmaceutically acceptable salt thereof and optionally (b) one or more mood stabilizers and one or more antidepressants (e.g., one antidepressant) other than agomelatine. In one embodiment, the patient prior to treat-ment with the combination of (a) agomelatine (or a prodrug or salt thereof) and (b) the one or more mood stabilizers and/or antidepressants was not treated with a mood stabilizer and/or antidepressant. In one embodiment, the EEG mea-sures are taken with resting eyes closed (REC).

Yet another aspect of the invention is an EEG device with a reduced number of electrodes that comprises (i) includes no more than 18 electrodes, (ii) comprises four or more electrodes from around the circumference of the head of the patient, and (iii) two or more electrodes from the midline of the head of the patient. In one embodiment, the configura-tion comprises (i) four or more electrodes selected from Fp1, Fp2, F7, F8, T3, T4, T5, T6, O1, and O2 and (ii) two or more electrodes selected from Fz, Cz, and Pz, according to the 10-20 system of electrode placement. In another embodi-ment, the configuration comprises (i) four or more elec-trodes selected from Fp1, Fp2, AF7, AF8, F7, F8, FT7, FT8, T7, T8, TP7, TP8, P7, P8, PO7, PO8, O1, and O2 and (ii) two or more electrodes selected from Fpz, AFz, Fz, FCz, Cz, CPz, Pz, POz, and Oz, according to the 10-10 system of electrode placement. In yet another embodiment, the elec-trode configuration is (i) a 7-channel electrode configuration consisting of electrodes at F7-Fz-F8-Cz-P7-Pz-P8, (ii) an 8-channel electrode configuration consisting of electrodes at F7-Fz-F8-Cz-P7-Pz-P8-Oz, (iii) an 8-channel electrode con-figuration consisting of electrodes at F7-Fz-F8-Cz-P7-Pz-P8-Fpz, (iv) an 8-channel electrode configuration consisting of electrodes at F7-Fz-F8-Cz-P7-Pz-P8-AUX, where the auxiliary (AUX) channel is a general electrophysiology channel, or (v) a 6-channel electrode configuration consist-ing of electrodes at Cz-Pz-Fp1-Fp2-P7-P8, according to the 10-10 system of electrode placement. The EEG device typically includes a head-worn sensor positioning frame (such as a cap, net, or headset) and electrodes, which are positioned appropriately within the frame according to one of the aforementioned electrode configurations.

In one embodiment, the EEG device has a 7-channel electrode configuration consisting of electrodes at F7-Fz-F8-Cz-P7-Pz-P8, according to the 10-10 system of electrode placement.

In another embodiment, the EEG device has an 8-channel electrode configuration consisting of electrodes at F7-Fz-F8-Cz-P7-Pz-P8-Oz, according to the 10-10 system of elec-trode placement.

In another embodiment, the EEG device has an 8-channel electrode configuration consisting of electrodes at F7-Fz-F8-Cz-P7-Pz-P8-Fpz, according to the 10-10 system of electrode placement.

In another embodiment, the EEG device has an 8-channel electrode configuration consisting of electrodes at F7-Fz-F8-Cz-P7-Pz-P8-AUX, according to the 10-10 system of electrode placement, where the auxiliary (AUX) channel is a general electrophysiology channel.

In yet another embodiment, the EEG device has a 6-chan-nel electrode configuration consisting of electrodes at Cz-Pz-Fp1-Fp2-P7-P8, according to the 10-10 system of electrode placement.

BRIEF DESCRIPTION OF THE DRAWINGS

For a more complete understanding of the present inven-tion, including features and advantages, reference is now made to the detailed description of the invention along with the accompanying figures.

DETAILED DESCRIPTION OF THE INVENTION

Figure 1:
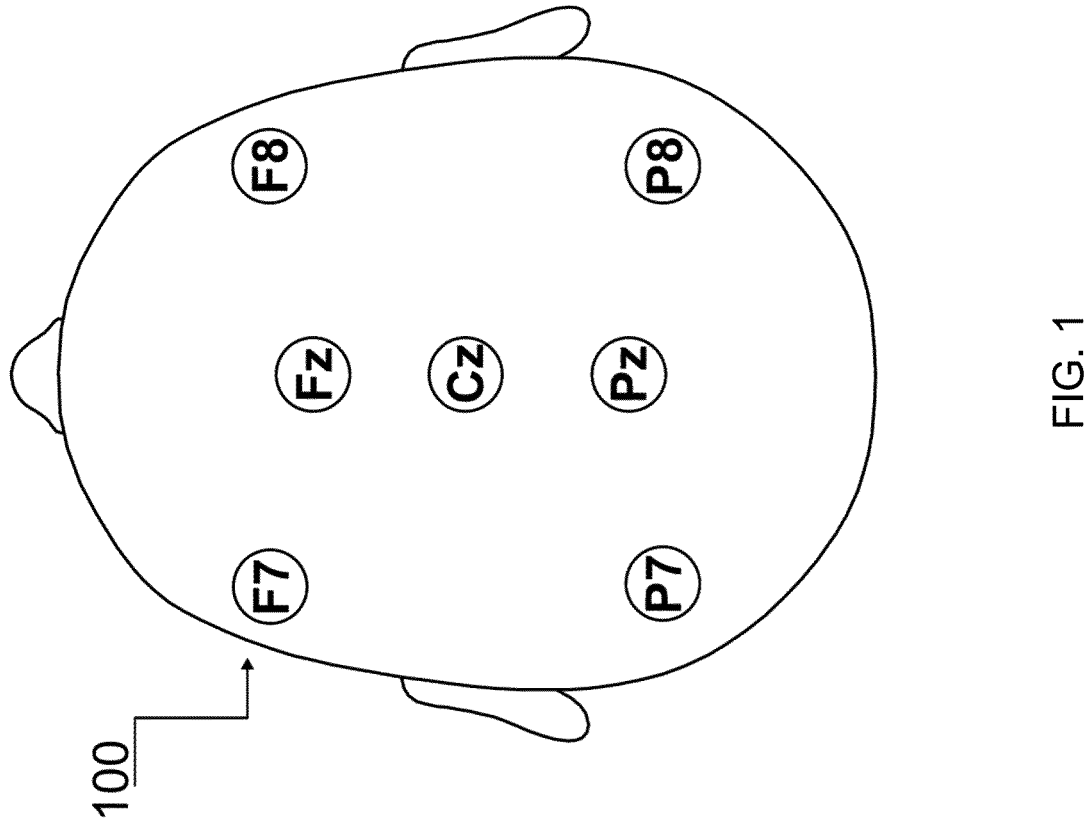
FIG. 1 is a diagram showing EEG electrode placement of the electrodes in the 7-channel electrode configuration of the present invention according to the standard 10-10 system.

It is to be understood that the figures and descriptions of the present disclosure may have been simplified to illustrate elements that are relevant for a clear understanding of the present disclosure, while eliminating, for purposes of clarity, other elements found in a typical wearable assistance device or typical method of using a wearable assistance device. Those of ordinary skill in the art will recognize that other elements may be desirable and/or required in order to implement the present disclosure. However, because such elements are well known in the art, and because they do not facilitate a better understanding of the present disclosure, a discussion of such elements is not provided herein. It is also to be understood that the drawings included herewith only provide diagrammatic representations of the presently preferred structures of the present disclosure and that structures falling within the scope of the present disclosure may include structures different than those shown in the drawings. Reference will now be made to the drawings wherein like structures are provided with like reference designations.

EEG electrode placements or positions on the brain (also referred to herein as "channels") are typically labeled using a letter or letters and a number, as seen in FIG. 1, for example. The letter of each electrode position stands for the general brain region that the electrode would cover. From front (nasion) to back (inion), each electrode letter labeling is as follows: Fp (pre-frontal or frontal pole), F (frontal), C (central line of the brain), T (temporal), P (parietal), and O (occipital). Electrode positions lying between these lines combine multiple letters, ordered from front to back. The number of the electrode gives information about the distance from the electrode to the midline of the brain. At the midline, the electrodes are labeled with a 'z' to represent zero. The electrode numbers increase as you move away from the midline. Odd numbers represent electrodes on the left hemisphere and even numbers represent electrodes on the right hemisphere.

The 10-20 system is an internationally recognized method that uses anatomical landmarks (i.e. nasion, inion, and preauricular points) to standardize the placement of EEG electrodes to record brain wave activity. The 10-20 system is based on the relationship between electrode location and the underlying area of the cerebral cortex while ensuring that all brain regions are covered. For the 10-20 system, the electrodes are placed at intervals of 10% or 20% of the total distance between the reference landmarks. For example, the distance from the nasion to the inion is measured, and electrodes are placed at 10% intervals along this line and 20% intervals along the line between the left and right ear. The 10-20 system allows for equal inter-electrode spacing and the electrode placements to be proportional to skull shape and size for a consistent and replicable method of recording EEG. Similarly, the 10-10 system is an internationally recognized extension of the 10-20 system nomenclature, placing electrodes in 10% intervals and therefore providing more detailed coverage of the scalp.

Electroencephalography (EEG) is a non-invasive way to record electrical activity of a patient's brain. EEG involves placing electrodes on the scalp to measure the brain's electrical signals, which can then be analyzed to understand brain function. It has now been found that the effects of a drug treatment, such as agomelatine treatment, can be predicted by a pattern of brain wave activity as recorded through EEG using a reduced electrode configuration compared to the full 19 channels in the 10-20 system of electrode placement or a similar subset of the 10-10 system. The reduction in the number of electrodes will increase the use of EEG as a tool for selecting therapies by decreasing the time to perform an EEG and the discomfort to patients, and increasing the ease to perform such an EEG.

EEG Device

One aspect of the invention is an EEG device 10 with a reduced number of electrodes comprising (or consisting essentially of or consisting of) (i) includes no more than 18 electrodes (e.g., no more than 18 electrodes or no more than 15 electrodes), (ii) comprises four or more electrodes from around the circumference of the head of the patient, and (iii) two or more electrodes from the midline of the head of the patient. In one embodiment, the configuration includes no more than 9 electrodes (such as no more than 8 electrodes, for example the configuration includes 6, 7, or 8 electrodes). In one embodiment, the configuration comprises (i) four or more electrodes selected from Fp1, Fp2, F7, F8, T3, T4, T5, T6, O1, and O2 and (ii) two or more electrodes selected from Fz, Cz, and Pz, according to the 10-20 system of electrode placement. In another embodiment, the configuration comprises (i) four or more electrodes selected from Fp1, Fp2, AF7, AF8, F7, F8, FT7, FT8, T7, T8, TP7, TP8, P7, P8, PO7, PO8, O1, and O2 and (ii) two or more electrodes selected from Fpz, AFz, Fz, FCz, Cz, CPz, Pz, POZ, and Oz, according to the 10-10 system of electrode placement. In yet another embodiment, the electrode configuration is (i) a 7-channel electrode configuration consisting of electrodes at F7-Fz-F8-Cz-P7-Pz-P8, (ii) 8-channel electrode configuration consisting of electrodes at F7-Fz-F8-Cz-P7-Pz-P8-Oz, (iii) 8-channel electrode configuration consisting of electrodes at F7-Fz-F8-Cz-P7-Pz-P8-Fpz, (iv) 8-channel electrode configuration consisting of electrodes at F7-Fz-F8-Cz-P7-Pz-P8-AUX, where the auxiliary (AUX) channel is a general electrophysiology channel, or (v) a 6-channel electrode configuration consisting of electrodes at Cz-Pz-Fp1-Fp2-P7-P8, according to a 10-10 system of electrode placement. As used herein, the term "reduced number of electrodes" refers to fewer electrodes than in a typical 10-20 electrode system or a similar 19 electrode subset of the 10-10 electrode placement system. The EEG device typically includes a head-worn sensor positioning frame (such as a cap, net, or headset) and the aforementioned electrodes, which are positioned appropriately within the frame. The frame is configured to be worn on a person's head.

In one embodiment, the EEG device may include one or more reference electrodes (such as one or two reference electrodes), for example on the earlobe or on the mastoid.

Figure 2:
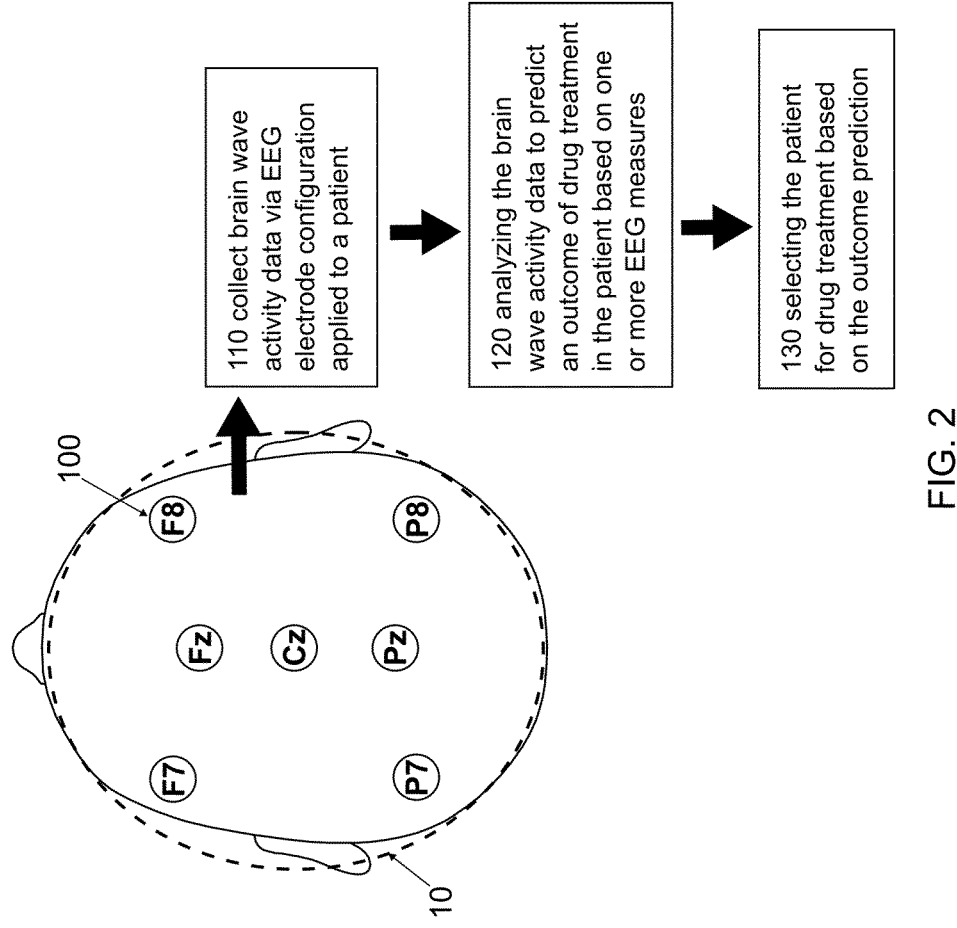
FIG. 2 is a diagram and flowchart showing a method of selecting a drug treatment for patients according to the present invention using the 7-channel electrode configura-tion.
Figure 4:
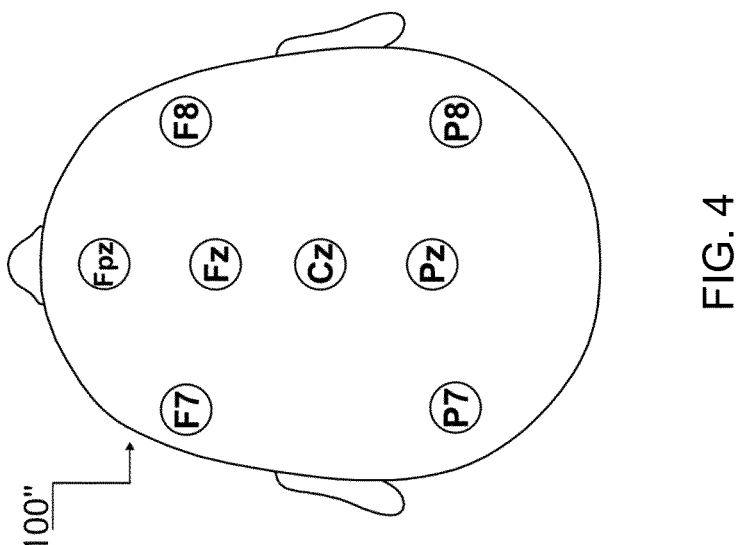
FIG. 4 is a diagram of showing the electrodes for an 8-channel electrode configuration of the present invention, where the eight channels include the seven from the 7-chan-nel electrode configuration as well as the Fpz electrode.
Figure 3:
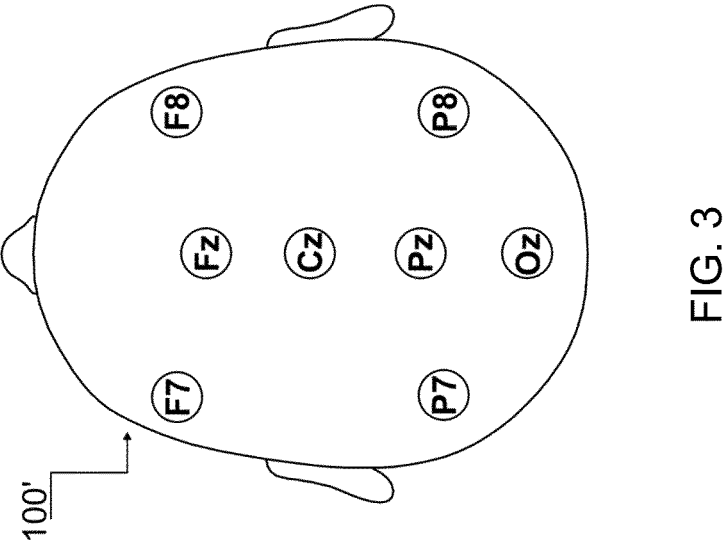
FIG. 3 is a diagram showing the electrodes for an 8-chan-nel electrode configuration of the present invention, where the eight channels include the seven from the 7-channel electrode configuration as well as the Oz electrode.
Figure 6:
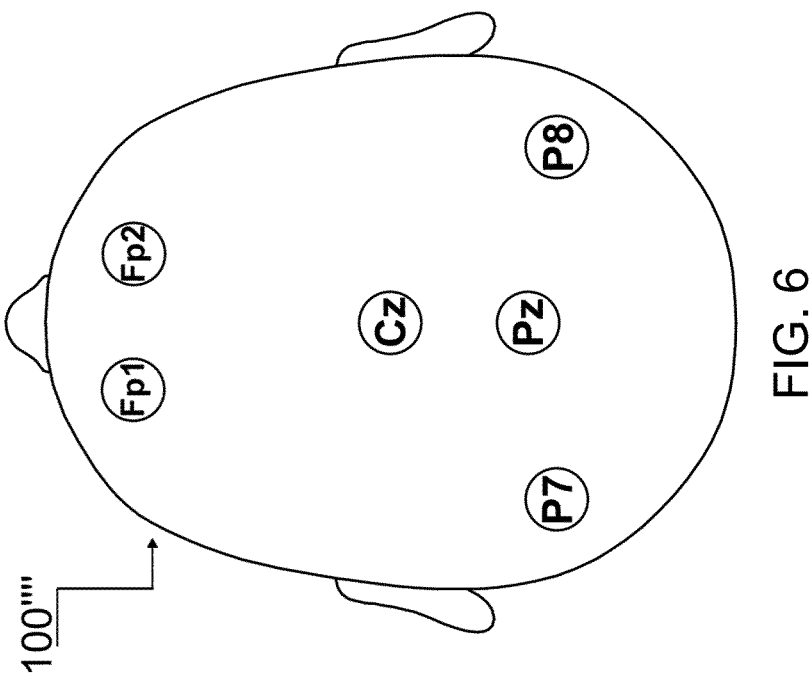
FIG. 6 is a diagram of showing the electrodes for a 6-channel electrode configuration of the present invention.
Figure 5:
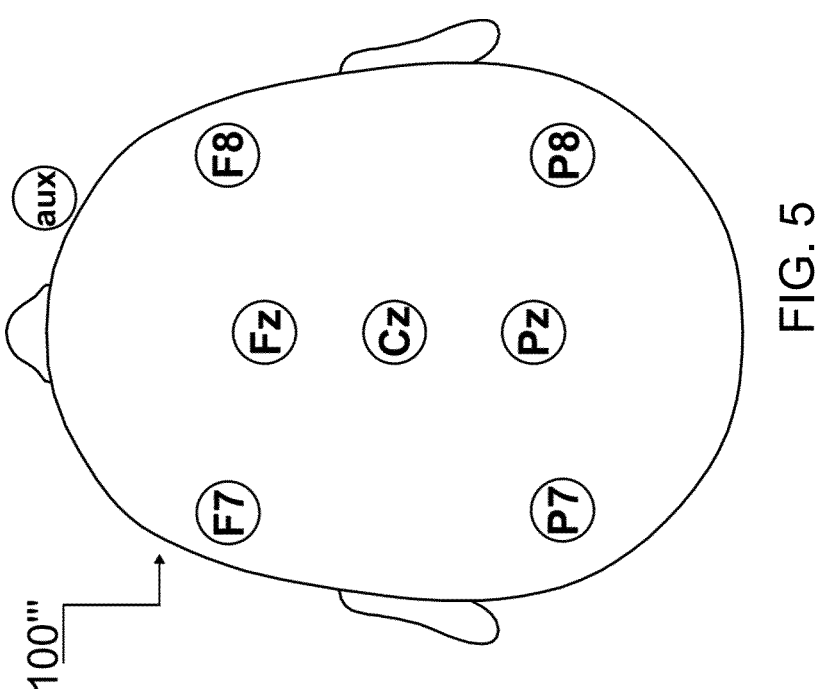
FIG. 5 is a diagram of showing the electrodes for an 8-channel electrode configuration of the present invention, where the eight channels include the seven from the 7-chan-nel electrode configuration as well as an auxiliary (AUX) channel, which is a general electrophysiology channel.

FIG. 2 illustrates the device 10 including the 7-channel electrode configuration (F7-Fz-F8-Cz-P7-Pz-P8), as well as a flowchart detailing a method of selecting a drug treatment based on the collected EEG data. As will be described in greater detail below, data from the device 10 can be collected and analyzed to select a patient for drug treatment, such as an agomelatine treatment, based on a predicted outcome.

The EEG device 10 may be the wearable device described in, for example, U.S. Pat. No. 9,814,426 or 11,172,859 or U.S. Patent Publication No. 2019/0380607, each of which is hereby incorporated by reference, where the number of electrodes is reduced to those described herein, such as the 7-channel, 8-channel (containing the 7 channels from the 7-channel configuration as well as either an Oz, Fpz, or an auxiliary channel that is a general electrophysiology channel), or 6-channel electrode configuration.

Figure 15:
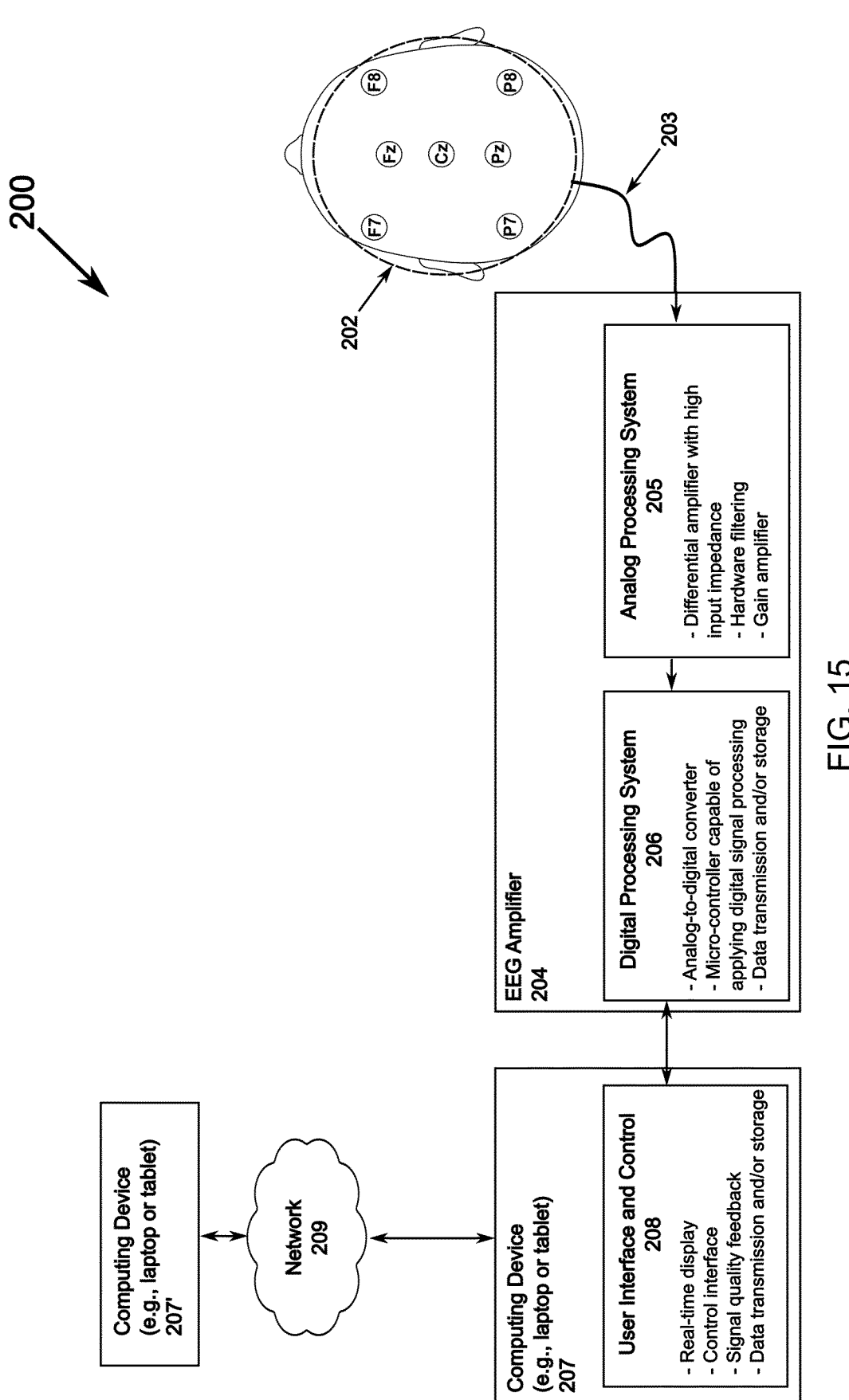
FIG. 15 is a block diagram of an EEG system for acquiring brain wave data from a patient, according to one or more embodiments of the present invention.

FIG. 15 is a block diagram of an EEG system 200 for acquiring brain wave data from a patient. The system includes 6, 7, or 8 electrodes, which are positioned on the patient's head with a cap, net or headset 202, according to the 6, 7, or 8-channel electrode configuration described herein. The electrodes are conductive and when positioned and engaged on (or in contact with) the scalp, measure the electrical potentials that arise on the surface of the head due to neuronal action within the brain. In one embodiment, the electrodes within the headset 202 have on their surface a conductive gel, paste, or solution to reduce electrical resistance between the electrodes and the scalp.

The system further includes an EEG amplifier 204 coupled to the electrodes via a communications link 203, such as a wired communications link (e.g., a wire or cable) or wireless communications link (e.g., WiFi, Bluetooth, or a cellular network). The EEG amplifier includes the analog processing system 205 connected to the digital processing system 206. In one embodiment, the EEG amplifier operates on data from eight electrode channels as well as the signal from (a) reference electrode(s), which may be placed on the earlobe or on the mastoid. In such a configuration, the eight electrode channels are online referenced to the earlobe or mastoid using a differential amplifier and then later re-referenced using the CAR.

The analog processing system 205 includes a differential amplifier with, for instance, high input impedance and a high common-mode rejection ratio, one or more hardware filters, and a gain amplifier. The differential amplifier amplifies the difference between the signal at each electrode and the reference electrode(s). The gain amplifier amplifies the signal to a more useful level. The filters can remove noise from the signals, act as a bandpass filter to pass specific frequency bands or manipulate select frequency bands. In one embodiment, the analog processing system 204 includes one or more four-channel amplifiers (such as two four-channel amplifiers).

The digital processing system 206 includes an analog-to-digital converter, a micro-controller capable of applying digital signal processing, a transmitter, and optionally data storage. The analog-to-digital converter converts the analog signals received from the analog processing system 204 to digital signals. In one embodiment, the analog-to-digital converter includes multiple analog-to-digital circuits located to service sets of the electrodes to convert the signals as close to the source as possible, which may reduce noise and interference. Furthermore, the digital processing system 206 may include hardware and/or software to execute Fast Fourier transform (FFT) calculations, coherence measurements and/or custom filtering The transmitter in the digital processing system 206 may communicate the digital signals to the user interface and control unit 208 running on a computing device 207 (e.g., a laptop or tablet). The user interface and control unit 208 may include a real-time display of the data being recorded, a control interface, and feedback on signal quality. It may also include data storage and data transmission via a network 209 to an alternate computing device 207' (e.g., a laptop, tablet, or cloud computing platform). When communicating over the Internet, the data may be encrypted to ensure confidentiality of the patient information. The calculation of one or more biomarkers relevant to selection of a drug treatment may either take place on the local computing device 207 or the secondary computing device 207' such as a cloud computing platform.

Drug Treatment Prediction

One aspect of the present invention is a method of selecting a drug treatment in a patient suffering from a psychiatric disorder (such as depression) that comprises collecting brain wave activity data via an electrode configuration of EEG electrodes applied to a patient (as shown in FIGS. 1-6); analyzing the brain wave activity data to predict an outcome of the drug treatment in the patient based on one or more EEG measures; and selecting the patient for drug treatment based on the outcome prediction. In an embodiment, the drug can be agomelatine. The electrode configuration should comprise (i) includes no more than 18 electrodes, (ii) comprises four or more electrodes from around the circumference of the head of the patient, and (iii) two or more electrodes from the midline of the head of the patient. In one embodiment, the configuration comprises (i) four or more electrodes selected from Fp1, Fp2, F7, F8, T3, T4, T5, T6, O1, and O2 and (ii) two or more electrodes selected from Fz, Cz, and Pz, according to the 10-20 system of electrode placement. In another embodiment, the configuration comprises (i) four or more electrodes selected from Fp1, Fp2, AF7, AF8, F7, F8, FT7, FT8, T7, T8, TP7, TP8, P7, P8, PO7, PO8, O1, and O2 and (ii) two or more electrodes selected from Fpz, AFz, Fz, FCz, Cz, CPz, Pz, POz, and Oz, according to the 10-10 system of electrode placement. In yet another embodiment, the electrode configuration is (i) a 7-channel electrode configuration consisting of electrodes at F7-Fz-F8-Cz-P7-Pz-P8 (see FIG. 1), (ii) an 8-channel electrode configuration consisting of electrodes at F7-Fz-F8-Cz-P7-Pz-P8-Oz (see FIG. 3), (iii) an 8-channel electrode configuration consisting of electrodes at F7-Fz-F8-Cz-P7-Pz-P8-Fpz (see FIG. 4), (iv) an 8-channel electrode configuration consisting of electrodes at F7-Fz-F8-Cz-P7-Pz-P8-AUX, where the auxiliary (AUX) channel is a general electrophysiology channel (see FIG. 5), or (v) a 6-channel electrode configuration consisting of electrodes at Cz-Pz-Fp1-Fp2-P7-P8 (see FIG. 6), according to the 10-10 system of electrode placement. This approach allows for more personalized and effective treatment strategies by leveraging advanced EEG data analysis techniques to understand complex brain activity and select treatment and patients who would most benefit from the treatment accordingly.

In one embodiment, the configuration may include one or two reference electrodes, for example on the earlobe or on the mastoid.

In one embodiment, the EEG measurements are taken while the patient is resting with eyes closed (REC). In another embodiment, the EEG measurements are taken while the patient is resting with eyes open (REO).

The psychiatric disorder may be a depressive disorder (such as major depressive disorder (MDD)), bipolar disorder (such as bipolar disorder I or bipolar disorder II), post-traumatic stress disorder (PTSD), schizophrenia, anhedonia-related aspects of schizophrenia (e.g., negative symptoms) and schizoaffective disorder (e.g., with mood and/or negative symptoms), or substance use disorder. In one embodiment, the psychiatric disorder is depression, such as major depressive disorder, the depressive phase of bipolar disorder or depressive symptoms in a psychiatric disorder, such as the depressive symptoms in PTSD.

The present invention may provide a machine learning-derived EEG biomarker associated with a specific pattern or feature in the EEG data that has been identified and validated using machine learning techniques to predict treatment outcomes. Exemplary machine learning techniques and processing of EEG data are described in U.S. Patent Publication No. 2021/0353224, which is hereby incorporated by reference, The EEG biomarker can be machine learning-derived, meaning machine learning algorithms are used to process and analyze the EEG data to identify specific patterns or features that serve as the biomarkers.

The biomarker may be predictive of effective agomelatine treatment, for example, for depressed patients, such as described in U.S. patent application Ser. No. 18/670,566, filed May 21, 2024, which is hereby incorporated by reference. In one embodiment, the biomarker for agomelatine efficacy is measured using resting-state EEG, which involves recording the brain's electrical activity while the patient is at rest, such as with their eyes closed (REC). The featured measurement for agomelatine efficacy in one embodiment is sample entropy, which reflects the complexity or irregularity of the EEG signal, in the low gamma frequency range (30-40 Hz). Higher sample entropy values indicate, as will be defined in greater detail below, more irregular brain rhythms, which are associated with better responses to agomelatine treatment. High EEG sample entropy in the low gamma frequency range (30-40 Hz) before treatment can be a predictor of a positive response to the medication.

The reduced electrode configurations described herein can be used in the methods of treatment and selection of patients described in U.S. patent application Ser. No. 18/670,566, filed May 21, 2024, which is hereby incorporated by reference.

The agomelatine treatment comprises administration of agomelatine, a prodrug thereof, or a pharmaceutically acceptable salt thereof.

Upon selection of agomelatine as an appropriate treatment, the method may further comprise administering agomelatine, a prodrug thereof, or a pharmaceutically acceptable salt thereof. In one embodiment of any of the methods described herein, the method comprises orally administering from about 25 to about 50 mg agomelatine, a prodrug thereof, or a pharmaceutically acceptable salt thereof (based on agomelatine free base) per day (preferably nightly). In one embodiment, the method comprises orally administering about 25 mg agomelatine, a prodrug thereof, or a pharmaceutically acceptable salt thereof (based on agomelatine free base) per day (preferably nightly). In another embodiment, the method comprises orally administering about 50 mg agomelatine, a prodrug thereof, or a pharmaceutically acceptable salt thereof (based on agomelatine free base) per day. In yet another embodiment, the method comprises orally administering about 30 mg agomelatine, a prodrug thereof, or a pharmaceutically acceptable salt thereof (based on agomelatine free base) per day.

In one embodiment of any of the methods described herein, the method comprises orally administering from about 25 to about 50 mg agomelatine per day. In a preferred embodiment, the method comprises orally administering from about 25 to about 50 mg agomelatine per day nightly.

In one embodiment of any of the methods described herein, the method comprises orally administering about 25 mg agomelatine per day. In a preferred embodiment, the method comprises orally administering about 25 mg agomelatine per day nightly.

In one embodiment of any of the methods described herein, the method comprises orally administering about 50 mg agomelatine per day. In a preferred embodiment, the method comprises orally administering about 50 mg agomelatine per day nightly.

In one embodiment of any of the methods described herein, the agomelatine is administered once daily at bedtime.

The psychiatric disorders described herein, such as major depressive disorder, bipolar disorder, bipolar I disorder, and bipolar II disorder, are intended to be as defined in the Diagnostic and Statistical Manual of Mental Disorders (DSM-5), which is hereby incorporated by reference. The severity of depression can be measured by the Montgomery-Åsberg Depression Rating Scale (MADRS), Patient Health Questionnaire-9 (PHQ-9), Clinical Global Impression-severity Scale (CGI-S), Hamilton Depression Rating Scale (HDRS), or any combination of any of the foregoing.

The terms "treat," "treatment," and "treating" in the context of the administration of a therapy to a patient refers to the reduction or inhibition of the progression and/or duration of a disease or condition, the reduction or amelioration of the severity of a disease or condition, and/or the amelioration of one or more symptoms thereof resulting from the administration of one or more therapies.

In certain embodiments, the patient previously had an inadequate response to other antidepressant therapy (i.e., one or more antidepressants other than agomelatine or a prodrug or salt thereof). In one embodiment, "inadequate response" as used herein refers to a patient experiencing a less than 50% reduction in depressive symptom severity from the start of initiating treatment. Typically, the inadequate response is during a current/active episode of the depression. In some embodiments, an inadequate response refers to a patient experiencing 0 to less than about 50% reduction in depressive symptom severity from the start of initiating treatment. In some embodiment, an inadequate response refers to a patient experiencing (a) less than about 50% reduction in depressive symptom severity from the start of initiating treatment and (b) at least a certain level of symptoms, such as a PHQ9 of at least 10. A patient's response may be measured by one or more scales described herein and/or by physician/clinical judgment. In some embodiments, an inadequate response is measured by ATRQ (the antidepressant treatment response questionnaire), MADRS, PHQ-9, CGI-S, or HDRS.

Agomelatine (N-[2-(7-methoxynaphthalen-1-yl)ethyl]acetamide) and its synthesis are described in European Patent Publication No. 447285 A1 and U.S. Pat. No. 5,225,442, both of which are hereby incorporated by reference in their entirety. Agomelatine is a melatonin agonist (i.e., MT1 and MT2 receptor-site agonism) and a 5HT2 antagonist.

The term "prodrug" refers to a precursor of a drug (such as agomelatine) that, following administration to a subject, yields agomelatine in vivo, such as via a chemical or physiological process such as solvolysis or enzymatic cleavage, or under physiological conditions (e.g., a prodrug on being brought to physiological pH is converted to agomelatine). Prodrugs may be prepared by modifying functional groups present on the compound in such a way that the modifications are cleaved, in vivo when the prodrug is administered to a subject. The modifications typically are achieved by synthesizing the drug (such as agomelatine) with a prodrug substituent. Prodrugs may be prepared as described in (i) Bundegaard, H. "Design of Prodrugs" p. 1-92, Elesevier, New York-Oxford (1985), (ii) Methods in Enzymology, Vol. 42, p. 309-396, edited by K. Widder, et al. (Academic Press, 1985), (iii) A Textbook of Drug Design and Development, 3rd Ed., Tailor & Francis Inc., edited by Krogsgaard-Larsen et al., Chapter 14 "Design and Application of Prodrugs," by Larsen et al., p. 460-514 (2002), (iv) H. Bundgaard, Advanced Drug Delivery Reviews, 8:1-38 (1992), (v) N. M. Nielsen, et al., *Journal of Pharmaceutical Sciences,* 77:285-298 (1988), and (vi) N. Kakeya, et al., *Chem. Pharm. Bull.,* 32:692-698 (1984), each of which is specifically incorporated herein by reference. In one embodiment, the prodrug substituent directs the compound to the lymphatic system. Such prodrug substituents are described in International Publication Nos. WO 2019/046491 and WO 2021/159021, each of which is hereby incorporated by reference. Such prodrug substituents may be conjugated to agomelatine through, for example, the methoxy or acetamide group of agomelatine.

The term "antidepressant" unless indicated otherwise includes selective serotonin reuptake inhibitors (SSRIs) (e.g., fluoxetine, escitalopram, citalopram, and sertraline), selective serotonin and norepinephrine reuptake inhibitors (SNRIs) (e.g., venlafaxine, duloxetine, and milnacipran), norepinephrine and dopamine reuptake inhibitors (e.g., bupropion), atypical antidepressants, and any combination of any of the foregoing. In one embodiment, the antidepressant is selected from an SSRI, SNRI, or bupropion or a pharmaceutically acceptable salt thereof. In another embodiment, the antidepressant is selected from an SSRI (other than fluvoxamine), SNRI, or bupropion or a pharmaceutically acceptable salt thereof.

The "mood stabilizer" referenced herein may be lithium carbonate, lithium orotate, lithium salt, valproic acid, divalproex sodium, propranolol, clonazepam, sodium valproate, lamotrigine, carbamazepine, gabapentin, oxcarbazepine, topiramate, a pharmaceutically acceptable salt thereof, or any combination of any of the foregoing.

As used herein, the term "high EEG sample entropy" refers to an EEG signal in which sample entropy is in the higher range of the distribution in patients, e.g., relative to the mean entropy value in a healthy population. Sample entropy is a statistical measure used to quantify the amount of regularity and unpredictability in time-series data, such as EEG signals. This is useful for analyzing non-linear and non-stationary signals like those produced by the brain. In one embodiment, EEG sample entropy is calculated as a standardized score (e.g., z-scores, T-scores, Standard Scores, Scaled Scores, Percentile rank, or Stanine scores) normalizing the patient against a healthy population (e.g., with respect to age, gender, or education). For example, the subject may have EEG sample entropy more than the mean of a similar healthy subject with a z-score more than zero, more than $z=0.25$, $z=0.5$, $z=0.75$, $z=1$, $z=1.5$, or $z=2$ (e.g., with a z-score of from about 0.5 or 0.75 to about 1 or 2, or a z-score of from about 0.75 or 1 to about 2). In one embodiment, a patient is considered to have higher entropy when the z-score is at least 0, 0.5, 1.0, 1.5, or 2.0 (e.g., at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0). In one embodiment, the raw EEG data from a patient is first loaded and subjected to preprocessing steps including resampling, trimming the recording, and/or applying notch and/or bandpass filtering. Subsequently, the data undergoes bad-channel rejection, bad-channel interpolation, and artifact rejection. Lastly, the data is filtered again and re-referenced using a common average reference. The data is quality-checked, and if it passes quality criteria, it is stored for analysis. This re-referenced data from the Pz electrode is used for calculating sample entropy in the low-gamma band. High sample entropy indicates a high level of irregularity or complexity in the EEG signal (Delgado-Bonal and Marshak, *Entropy* (Basel), 2019, 21 (6): 541, doi: 10.3390/e21060541, PMID: 33267255). This means the brain activity is less predictable and more chaotic.

Sample entropy is a modified version of approximate entropy, which is a modification of the Kolmogorov-Sinai (KS) entropy (Delgado-Bonal and Marshak, 2019, supra). KS entropy directly relates to the "entropy rate" of a dynamic system, which measures how much information over time (on average) is needed to describe a process. However, KS entropy can only be practically calculated for well-defined systems without any measurement noise and vast amounts of data. Approximate entropy solves this problem with a basis in the same principles as KS entropy, but usable with real data (Pincus, PNAS, 1991, 88 (6): 2297-301, doi: 10.1073/pnas.88.6.2297, PMID: 11607165). Approximate entropy measures the frequency rate that a snippet of data of fixed length is approximately repeated and then also remains similar for the next sample. Approximate entropy is known to be a biased measurement, especially with small amounts of data. Sample entropy is a very similar measure to approximate entropy but modified to solve this problem (Delgado-Bonal and Marshak, 2019, supra). Channel-wise EEG sample entropy was therefore calculated in the following analyses.

As used herein, the terms "subject" and "patient" are used interchangeably and refer to a human patient unless indicated otherwise. In one embodiment, the patient has moderate to severe major depressive disorder. In another embodiment, the patient has moderate to severe major depressive disorder and is currently being treated with a SSRI, SNRI, or bupropion (e.g., bupropion or a pharmaceutically acceptable salt thereof in combination with another medication, such as dextromethorphan) for at least 6 weeks with no dose modifications in the past 2 weeks. In yet another embodiment, the patient has moderate to severe major depressive disorder and has failed to adequately respond to the current antidepressant medication which includes a SSRI, SNRI, or bupropion (e.g., bupropion or a pharmaceutically acceptable salt thereof in combination with another medication, such as dextromethorphan) for at least 6 weeks with no dose modifications in the past 2 weeks.

EEG measures indexing neural complexity include, but are not limited to, Higuchi's Fractal Dimension, Katz's Fractal Dimension, Detrended Fluctuation Analysis, Largest Lyapunov Exponent, Approximate Entropy, Sample Entropy, Multiscale Entropy, Modified Multiscale Entropy, and Aperiodic Exponent. Such measures are described in Lau et al., *Eur J Neurosci,* 2022, 56 (7): 5047-5069; doi: 10.1111/ejn. 15800; PMID 35985344), which is hereby incorporated by reference.

The Pz electrode refers to a specific placement of an electrode on the scalp used in electroencephalography (EEG). "Pz" stands for "parietal zero," indicating its location at the midline of the parietal region of the scalp. This electrode placement is part of the international 10-20 and 10-10 systems, which are standardized methods for placing electrodes on the scalp to ensure consistent and accurate recording of brain activity. The Pz electrode is used in the EEG montages described herein to monitor and record electrical activity in the brain. In one embodiment, the signal from the Pz electrode is re-referenced using a common average reference from all electrodes in the reduced electrode configuration. In another embodiment, the signal from the Pz electrode is re-referenced using a common average reference either from the 7 electrodes (F7, Fz, F8, Cz, P7, Pz, P8) from the 7-channel configurations described herein or from the 6 electrodes (Cz, Pz, Fp1, Fp2, P7, P8) from the 6-electrode configuration described herein and then the re-referenced signal is used for calculating EEG measurements, such as sample entropy. In another embodiment, the signal from the Pz electrode is re-referenced using a common average reference from the 7 electrodes (F7, Fz, F8, Cz, P7, Pz, P8) from an 8-channel configuration described herein.

In accordance with the present invention, the EEG measurements are performed with electrodes placed in a reduced electrode configuration, that is at a reduced number of electrode channels (or reduced number of electrodes) related to a conventional 10-20 system or similar 19 channel subset of the 10-10 electrode placement system. The conventional 10-20 system uses 19 electrode channels at Fp1, Fp2, F7, F8, F3, F4, Fz, T3, T4, C3, C4, Cz, T5, T6, P3, P4, Pz, O1, and O2, and a similar subset from the 10-10 system uses 19 channels at Fp1, Fp2, F7, F8, F3, F4, Fz, T7, T8, C3, C4, Cz, P7, P8, P3, P4, Pz, O1, and O2. The reduced electrode configuration of the present disclosure-comprised of four or more electrodes from electrodes around the circumference of the head (which in the 10-20 system of electrode placement includes electrodes Fp1, Fp2, F7, F8, T3, T4, T5, T6, O1, and O2 and in the 10-10 system of electrode placement includes electrodes Fp1, Fp2, AF7, AF8, F7, F8, FT7, FT8, T7, T8, TP7, TP8, P7, P8, PO7, PO8, O1, and O2) and two or more electrodes from the midline (which in the 10-20 system of electrode placement includes electrodes Fz, Cz, and Pz and in the 10-10 system of electrode placement includes electrodes Fpz, AFz, Fz, FCz, Cz, CPz, Pz, POZ, and Oz)—can be used to create a common-average reference (CAR) that reduces global noise from the signal in a way similar to the 10-20 system or a comparable 19 channel subset of the 10-10 system. The reduced electrode configurations of the present disclosure achieve this while reducing the number of electrodes needed to collect the data, thereby decreasing complexity and cost and simplifying set up by using just a subset of the 19 channels. For example, the reduced electrode configuration of the present invention may be a 7-channel electrode configuration 100 consisting of electrodes at F7-Fz-F8-Cz-P7-Pz-P8 (see FIG. 1); an 8-channel electrode configuration 100' consisting of electrodes at F7-Fz-F8-Cz-P7-Pz-P8-Oz (see FIG. 3); an 8-channel electrode configuration 100" consisting of electrodes at F7-Fz-F8-Cz-P7-Pz-P8-Fpz (see FIG. 4); an 8-channel electrode configuration 100''' consisting of electrodes at F7-Fz-F8-Cz-P7-Pz-P8-AUX, where the auxiliary (AUX) channel is a general electrophysiology channel (see FIG. 5); or a 6-channel electrode configuration 100'''' consisting of electrodes at Cz-Pz-Fp1-Fp2-P7-P8 (see FIG. 6), according to the 10-10 system of electrode placement.

As illustrated in FIG. 2, a method of the present invention of selecting a drug treatment, such as an agomelatine treatment, in patients (e.g., depressed patients) may comprise collecting brain wave activity data at step 110 via one of the reduced electrode configurations described herein, such as the 7-channel electrode configuration 100, which may apply EEG electrodes to a patient via a wearable device 10; analyzing the brain wave activity data to predict an outcome of the agomelatine treatment in the patient based on one or more EEG measures (e.g. sample entropy) at step 120; and selecting the patient for agomelatine treatment based on the outcome prediction at step 130.

Embodiments of the present disclosure also include the aforementioned wearable device 10 that may be configured to incorporate any of the above reduced electrode configurations for application to the patient to collect EEG data. For example, the device may be a cap and/or headset made out of a semi-rigid material that is fitted onto the patient's head and includes the reduced number of electrodes of the reduced electrode configurations 100 in FIG. 2 (7-channel), 100' in FIG. 3 (8-channel), 100" in FIG. 4 (8-channel), 100''' in FIG. 5 (8-channel), or 100'''' in FIG. 6 (6-channel).

The one or more EEG measures are selected from EEG measures of entropy or complexity, and any combination thereof. The one or more EEG measures can be EEG sample entropy at the Pz electrode. The one or more EEG measures can be measures of predictability, measures of regularity, or any combination thereof. The one or more EEG measures can be selected from approximate entropy, detrended fluctuation analysis, Higuchi fractal dimension, Katz fractal dimension, largest Lyapunov exponent, modified multiscale entropy, multiscale entropy, aperiodic exponent, and any combination thereof.

The one or more EEG measures can be analyzed with stored historical subject data containing data from a plurality of subjects having a psychiatric disorder (e.g., a depressive disorder), who received treatment with the drug treatment (e.g., agomelatine, a prodrug thereof, or a pharmaceutically acceptable salt thereof), wherein the stored historical subject data include for a plurality of the subjects, the efficacy of the drug treatment (e.g., agomelatine treatment) and one or more of the same type of EEG measures as calculated for the patient.

The step of analyzing the brain wave activity data to predict an outcome of the drug treatment in the patient comprises determining a drug efficacy likelihood score for the patient based on the stored historical subject data; and selecting the patient based on the likelihood score.

Appropriate biomarkers, such as characteristics that indicate the suitability of a drug treatment, can be identified by methods known in the art.

The EEG data can be pre-processed (e.g., for quality control purposes) as follows. First, the signal can be resampled, trimmed, and filtered. Second, artifact handling can be performed to reject channels with high amplitude, interpolate rejected channels, and/or reject epochs with high amplitude. In the 8-channel configuration embodiments herein, artifact handling can be improved with additional information either from the Fpz channel or the auxiliary (AUX) channel, for those respective configurations. Alpha characterization is enhanced by the Oz channel in the 8-channel configuration embodiment containing channels F7-Fz-F8-Cz-P7-Pz-P8-Oz described herein. The data can then be post-processed wherein filters are applied and the signals are re-referenced with the common average. The common average can be calculated by averaging the temporal signal across the reduced electrode configuration (e.g. 7-channel configuration (F7, Fz, F8, Cz, P7, Pz, and P8)). For agomelatine, the signal from the Pz electrode can be re-referenced with the common average by subtracting the average signal from all electrodes from the Pz electrode signal.

An EEG measure or feature (e.g., low gamma sample entropy at the Pz electrode) can be calculated using the data after the above processing steps. Feature values that lie outside of a confidence interval (e.g., the 95% confidence interval) of the reference dataset can be rejected as outliers. The feature values can be normalized with respect to a large reference dataset of healthy control subjects, which transforms them to a z-scored value. If no REC sessions for a given participant were marked as outliers, the biomarker can be calculated by taking the average of the normalized feature values across the two baseline (or more) REC sessions.

A likelihood score can be determined based on whether the biomarker value is above or below a predetermined positive threshold. For example, if the biomarker value is above a positive threshold, the patient is biomarker positive and should be selected for treatment. If the biomarker value is below a negative threshold, the patient is biomarker negative and should not be selected for treatment.

In another embodiment, the one or more EEG measures are analyzed with stored historical subject data containing data (e.g., de-identified or otherwise anonymized data) from a plurality of subjects having a psychiatric disorder (e.g., major depressive disorder or bipolar disorder) who received treatment with the drug (e.g., agomelatine, a prodrug thereof, or a pharmaceutically acceptable salt thereof). The data may include for a plurality of the subjects, the efficacy of the drug (e.g., agomelatine) treatment and one or more of the same type of EEG measures as calculated for the patient.

In one embodiment, the analysis includes determining a drug (e.g., agomelatine) efficacy likelihood score (e.g., z-score) for the patient based on the stored historical subject data, and then selecting a patient where the patient is predicted to be responsive to the drug based on the likelihood score. The likelihood score may be binary (that is, either 0 or 1) or continuous (that is, any decimal value within a range of possible score values). In one embodiment, the likelihood score is bounded, for example, any value from 0.0 to 1.0.

Determination of Reduced Electrode Configurations

A current agomelatine biomarker (sample entropy) was calculated using the signal from the Pz electrode after it was re-referenced using a common average reference (CAR) consisting of all nineteen electrodes in a custom configuration of the Neuroelectrics Enobio 20 system, which were a subset of the 10-10 montage (using channels Fp1, Fp2, F7, F8, F3, F4, Fz, T7, T8, C3, C4, Cz, P7, P8, P3, P4, Pz, O1, and O2). The signal from two resting eyes-closed (REC) recordings were averaged to determine the biomarker value.

The inventors analyzed whether configurations using subsets of the 19 channels could maintain the robustness of the agomelatine biomarker while reducing the number of electrodes needed, thus decreasing the device complexity and cost, while increasing the ease of setup. The signal from the electrode of interest (e.g., Pz in the case of the agomelatine biomarker) is re-referenced using a common average reference (CAR) consisting of the averaged signal from all the electrodes in the configuration, which is intended to remove global noise from the signal. The inventors found that in order to adequately represent the global noise in the CAR, the electrode configuration needed to comprise four or more electrodes from the circumference of the head (which in the 10-20 system of electrode placement includes electrodes Fp1, Fp2, F7, F8, T3, T4, T5, T6, O1, and O2 and in the 10-10 system of electrode placement includes electrodes Fp1, Fp2, AF7, AF8, F7, F8, FT7, FT8, T7, T8, TP7, TP8, P7, P8, PO7, PO8, O1, and O2) as well as two or more electrodes from the midline (which in the 10-20 system of electrode placement includes electrodes Fz, Cz, and Pz and in the 10-10 system of electrode placement includes electrodes Fpz, AFz, Fz, FCz, Cz, CPz, Pz, POz, and Oz). The inventors found, for example, that a 7-channel electrode configuration (containing channels F7, Fz, F8, Cz, P7, Pz, and P8) maintained signal quality while also reducing the number of electrodes needed by over half.

First, on a set of baseline EEG data from an unrelated drug where the same Enobio 20 EEG recording system (available from Neuroelectrics in Barcelona, Spain) was used, the inventors evaluated 16 different subset configurations on their similarity to the 19-channel CAR signal. The inventors performed pre-processing, a quality control check, and a CAR using only the channels in the subset and then looked at the similarity to the original agomelatine biomarker (Spearman correlation of low gamma sample entropy at the Pz electrode after re-referencing) and similarity of the re-referenced signal at the Pz electrode through spectral features (Spearman correlation of center frequency of the alpha peak and of aperiodic exponent) and relative power (Spearman correlation of relative broadband power and of relative power in low-gamma).

Half of the data from one agomelatine study (balanced for age and gender) were used for further hypothesis formalization as a training set. The inventors reviewed previously explored metrics, as well as the clinical relevance (Spearman correlation between low gamma sample entropy at the Pz electrode after re-referencing and percent and absolute change in the MADRS score) and the reliability (concordance correlation of low gamma sample entropy at the Pz electrode after re-referencing between two 4-minute REC sessions) of the biomarker. The inventors found, for example, that the 7-channel configuration with electrodes F7, Fz, F8, Cz, P7, Pz, P8 performed better than the 7-channel configuration with electrodes F3, Fz, F4, Cz, P3, Pz, P4, supporting the inventors' theory that to adequately represent the global noise in the CAR, the electrode configuration needed to comprise four or more electrodes from the circumference of the head as well as two or more electrodes from the midline.

Based on these results, three configurations were selected to complete further testing: a 7-channel configuration (F7-Fz-F8-Cz-P7-Pz-P8), a 6-channel configuration (Cz-Pz-Fp1-Fp2-P7-P8), and the ear-referenced data (not using a common average reference).

A test set consisted of the remaining 50% of recordings from the agomelatine study. Each of the remaining reduced electrode configurations was evaluated on a set of criteria required for a successful replacement of the 19-channel CAR configuration. FIGS. 7-10B show on this test set of data the comparison between the data when using the 19-channel CAR and the data when using a reduced electrode configuration CAR.

The criteria either were set in comparison with the biomarker (sample entropy in the low-gamma frequency band from the Pz electrode) calculated using the 19-channel CAR or in comparison with the signal from the Pz electrode re-referenced with the 19-channel CAR. The criteria included: consistency with the current biomarker (should meet 3 of the 5 factors in Table 1 below; correlation with current biomarker>0.80, precision>0.85, sensitivity>0.85, percent of the population whose biomarker status should have been negative but is now positive≤10%, percent of the population whose biomarker status should have been positive but is now negative≤ 10%), clinical relevance (correlation with percent change in MADRS from baseline to week 6≥ 19-channel CAR correlation with a 0.05 tolerance, correlation with absolute change in MADRS from baseline to week 6≥19-channel CAR correlation with a 0.05 tolerance), and feature reliability from the Pz electrode (concordance correlation coefficient (CCC) of the biomarker value between two 4-minute REC recordings within 0.2 of the reliability of the 19-channel CAR biomarker). Each configuration was also evaluated on similarity of the signal at the Pz electrode when re-referenced, including its spectral features (correlations of the center frequency of the alpha peak and the aperiodic exponent) and relative power (correlations of the relative broadband power and relative power in the lower gamma frequency band).

Table 1 below shows the comparison between the 19-channel CAR configuration and the test set data for each reduced electrode configuration (7-channel or 6-channel) or the ear reference.

TABLE 1

| Re-referencing Scheme | 7-channel (F7-FZ-F8-CZ-P7-PZ-P8) | 6-channel (CZ-PZ-FP1-FP2-P7-P8) | Ear-reference |
|---|---|---|---|
| Consistency with Current Biomarker (should meet 3 of 5): | | | |
| Correlation with current biomarker feature value above 0.80 | ✓ | ✓ | X |
| Precision (out of all predicted as positive, how many are really positive?) above 85% | ✓ | X | X |
| Sensitivity (out of all the people that have the biomarker, how many got positive results?) above 85% | ✓ | X | X |
| The percent of the population whose biomarker status should have been negative but is now positive should be at most 10% | ✓ | ✓ | X |
| The percent of the population whose biomarker status should have been positive but is now negative should be at most 10% | ✓ | ✓ | X |
| Clinical relevance: | | | |
| Correlation with percent change in MADRS from baseline to week 6 equal to or greater than the correlation the CAR biomarker had, with a 0.05 tolerance | ✓ | ✓ | ✓ |
| Correlation with absolute change in MADRS from baseline to week 6 equal to or greater than the correlation the CAR biomarker had, with a 0.05 tolerance | ✓ | ✓ | ✓ |
| Feature reliability from Pz electrode: | | | |
| CCC within 0.2 of the reliability of the CAR biomarker | ✓ | ✓ | ✓ |

Figure 7:
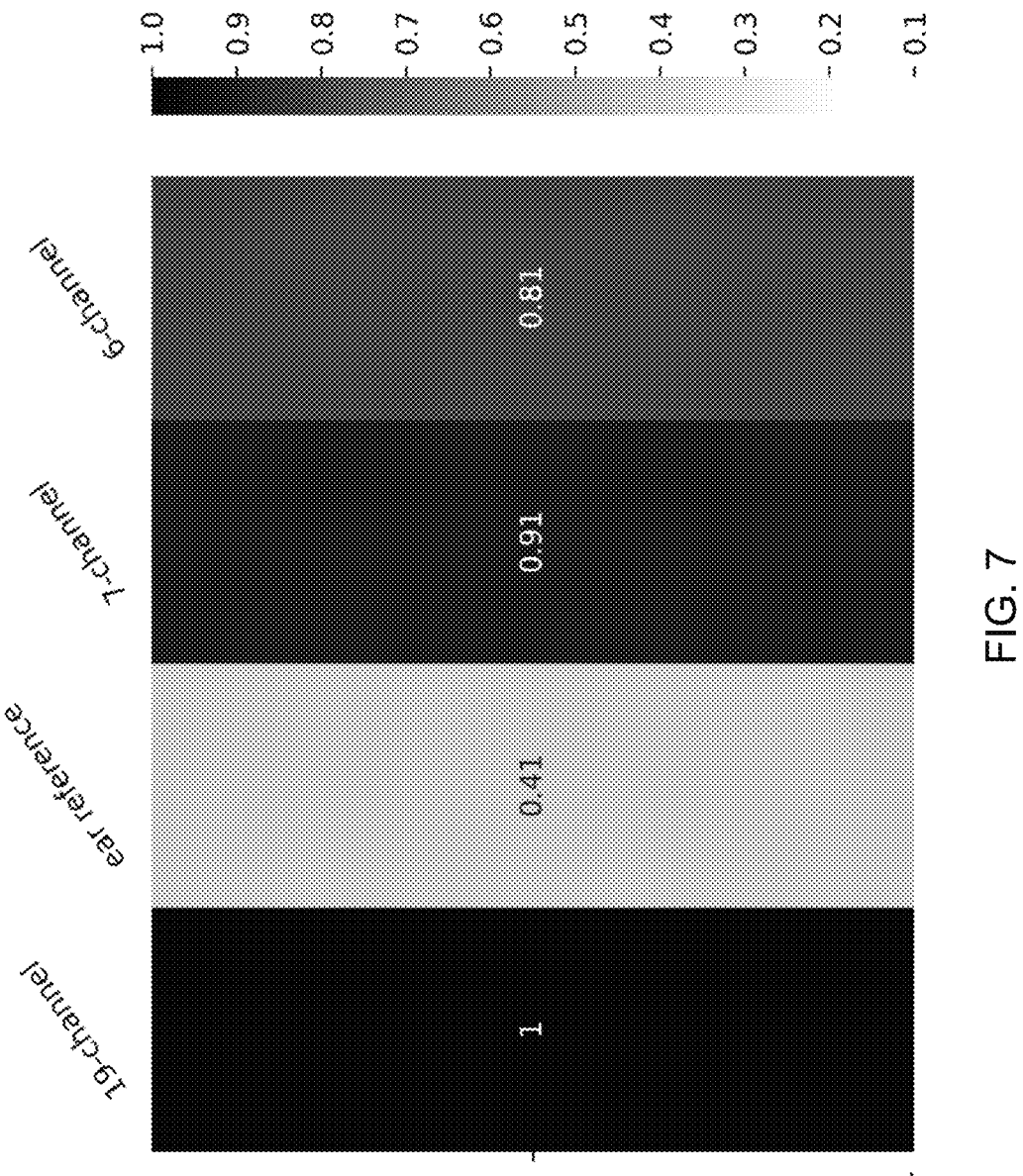
FIG. 7 is a table comparing, on a test set of data, the value of sample entropy in the low-gamma (30-40 Hz) band from the Pz electrode when re-referenced with a common average reference (CAR) using all 19 channels from a subset of the 10-10 system (referred to as the 19-channel biomarker value in the row label) to the value of sample entropy in the low-gamma band from the Pz electrode when referenced in a variety of ways. The value shown in each cell of the table is the spearman correlation coefficient. The biomarker when referenced using a 19-channel CAR is compared to (by column) itself, the original ear-referenced signal without using any CAR, the signal when using a CAR from the 7 channels in the 7-channel configuration of the present inven-tion, and the signal when using a CAR from the 6 channels in the 6-channel configuration of the present invention.
Figure 8B:
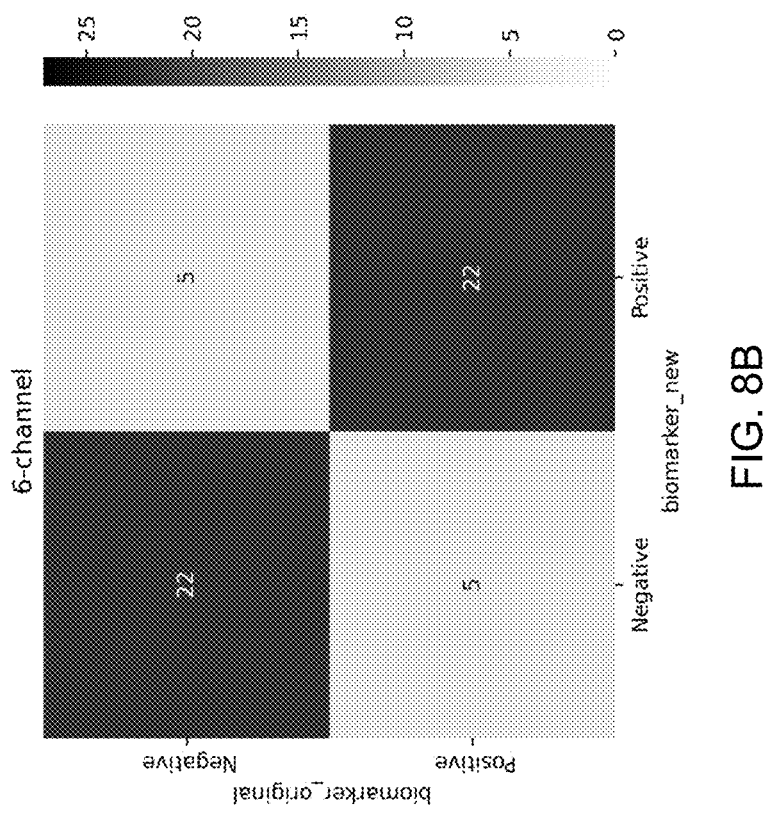
FIGS. 8A-C contains confusion matrices, from the test set of data, comparing biomarker status (either Positive or Negative) from when the biomarker was calculated using a 19-channel CAR (y-axis, "biomarker_original") to when the biomarker was calculated using (8A) a CAR from the 7 channels in the 7-channel configuration of the present invention, (8B) a CAR from the 6 channels in the 6-channel configuration of the present invention, or (8C) the original ear-referenced signal without any CAR (x-axis, "biomarker_new").
Figure 8A:
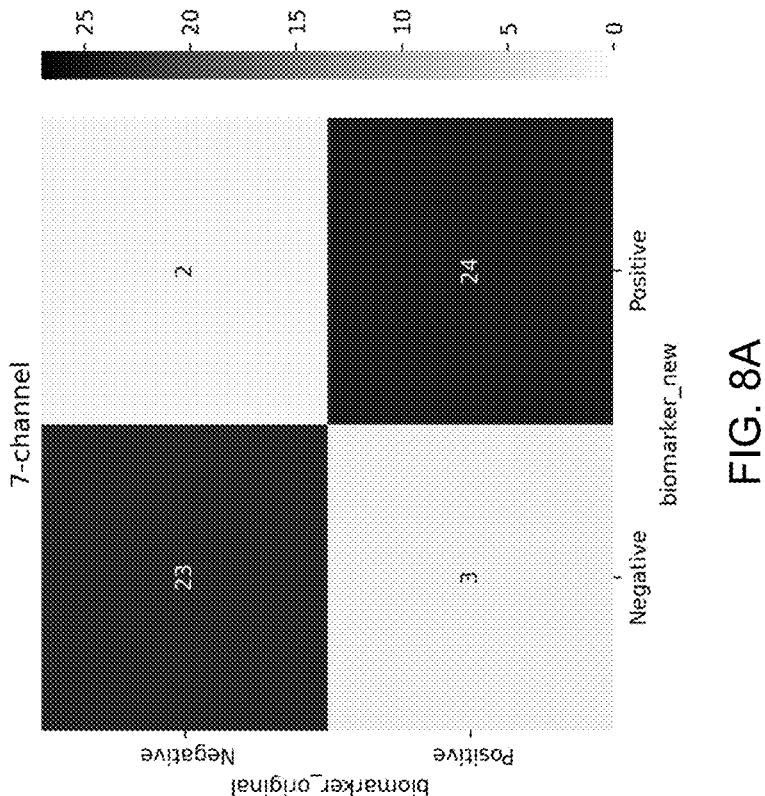
Figure 8C:
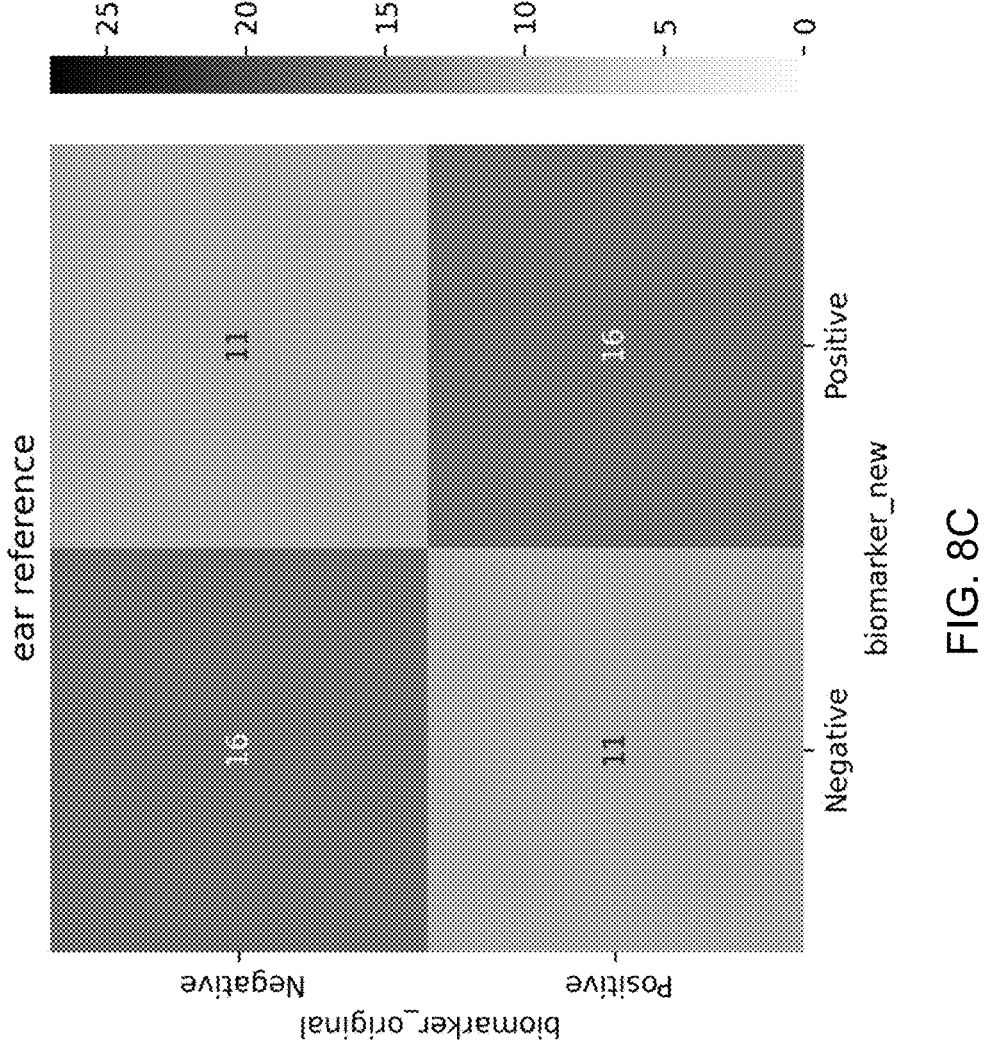
Figure 9A:
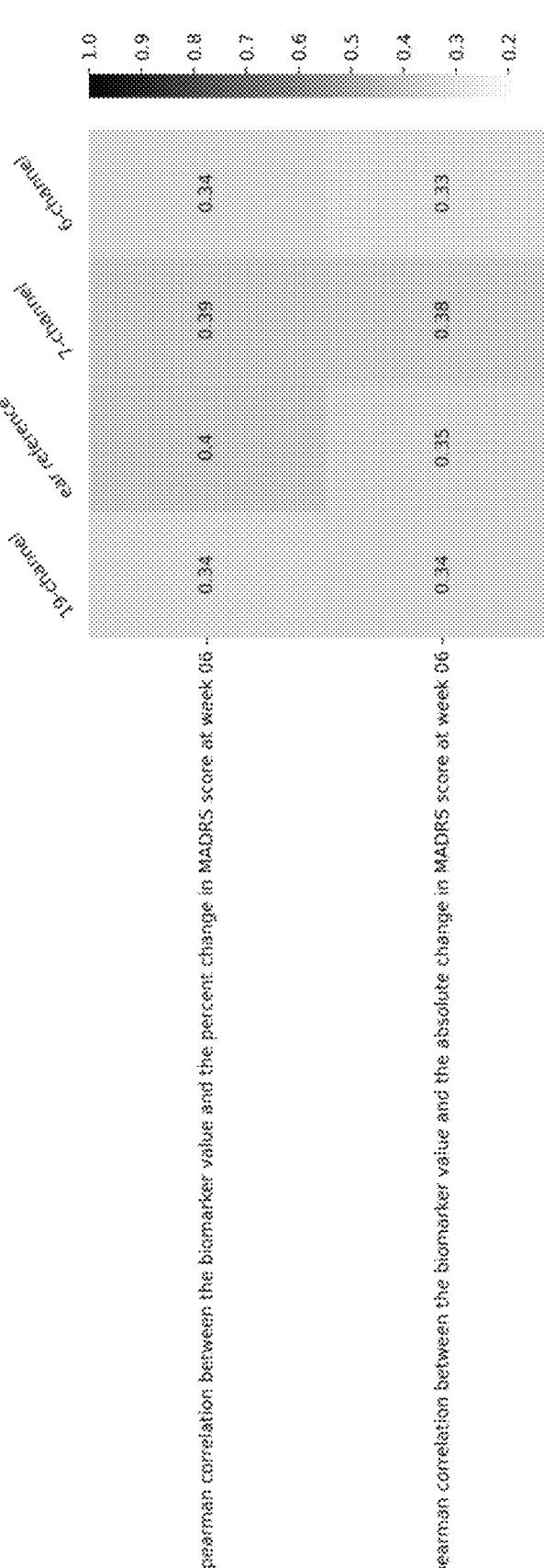
FIG. 9A is a table showing, for the test set of data, the correlation between the biomarker value and either the percent change in the Montgomery-Åsberg Depression Rating Scale (MADRS) between baseline and week 6 (top row) or the absolute change in the MADRS between baseline and week 6 (bottom row). Each column shows the spearman correlation coefficient when the biomarker value (sample entropy in the low-gamma band from the Pz electrode) is re-referenced in a different way (by column): using a 19-channel CAR, using the original ear-referenced signal without using any CAR, using the signal when using a CAR from the 7 channels in the 7-channel configuration of the present invention, and using the signal when using a CAR from the 6 channels in the 6-channel configuration of the present invention.
Figure 9B:
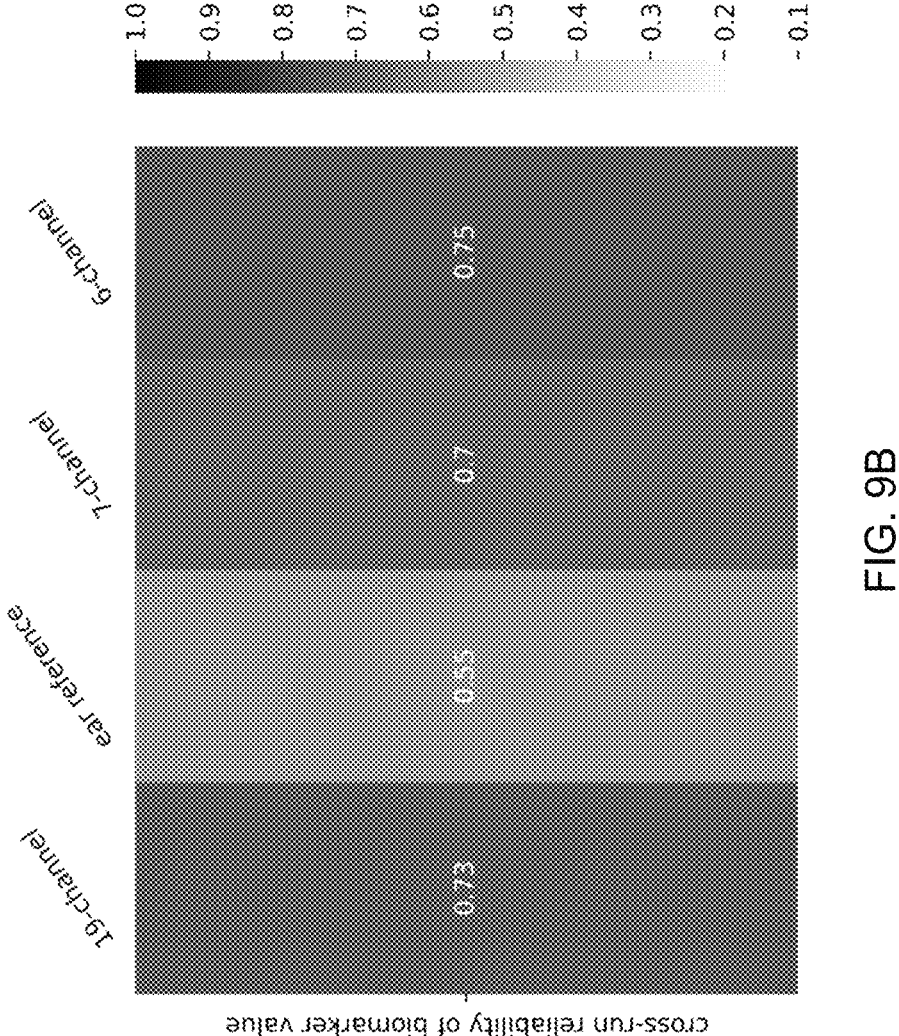
FIG. 9B is table showing, for the test set of data, the reliability of the biomarker value when calculated on two separate 4-minute resting eyes closed (REC) recordings. Each column shows the concordance correlation coefficient between the value from the two recordings when the biomarker value of sample entropy in the low-gamma band from the Pz electrode is re-referenced in different ways (by column): using a 19-channel CAR, using the original ear-referenced signal without using any CAR, using the signal when using a CAR from the 7 channels in the 7-channel configuration of the present invention, and using the signal when using a CAR from the 6 channels in the 6-channel configuration of the present invention.
Figure 10A:
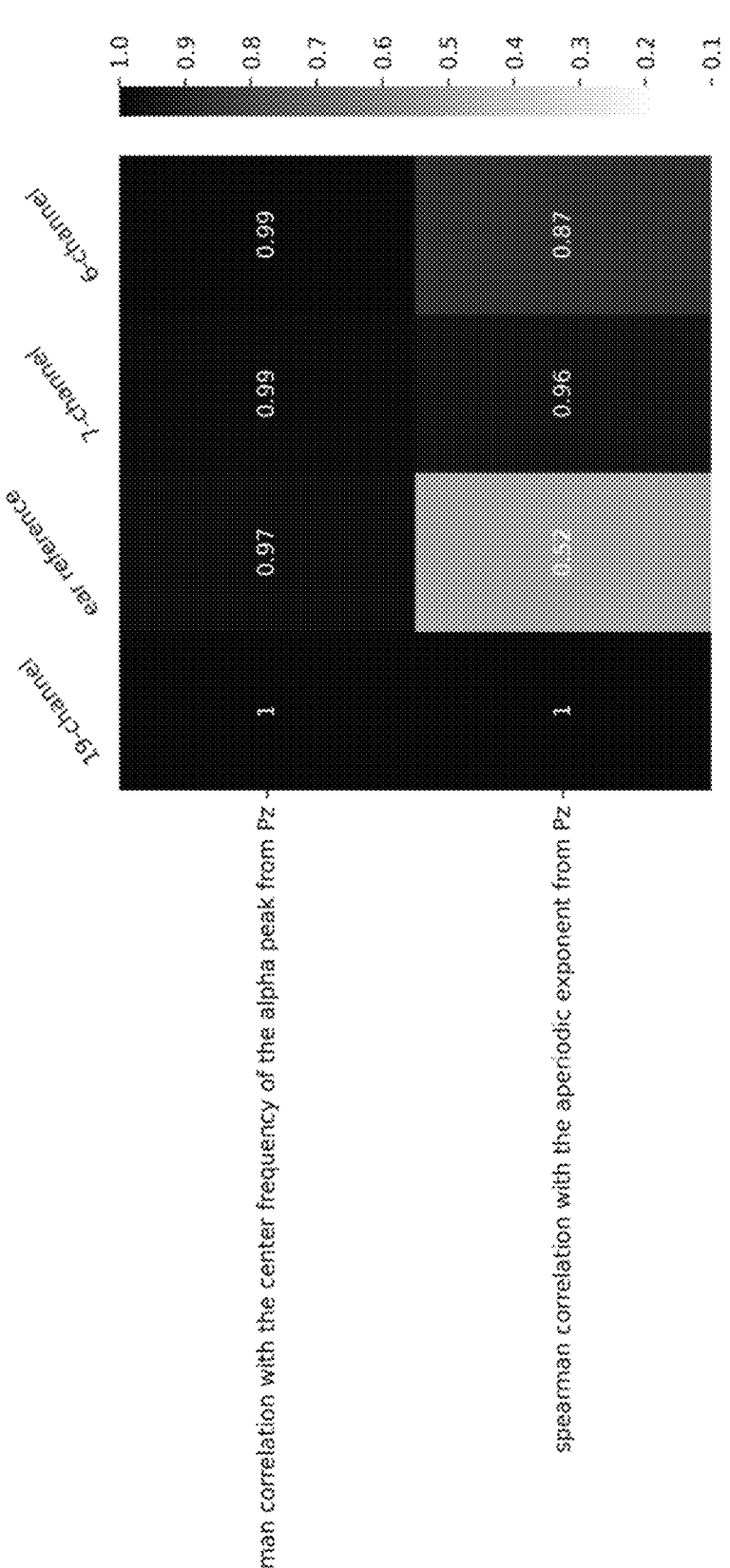
FIG. 10A is a table showing, for the test set of data, the correlation between spectral features of the signal from the Pz electrode when re-referenced with a CAR using all 19 channels from a subset of the 10-10 system to when it was re-referenced in a variety of ways. The value shown in each cell of the table is the spearman correlation coefficient. By row, either the center frequency of the alpha (between 7 and 14 Hz) peak (top) or the aperiodic exponent (bottom) from Pz using a 19-channel CAR is compared to (by column) itself, the value from the original ear-referenced signal without using any CAR, the value from using a CAR from the 7 channels in the 7-channel configuration of the present invention, and the value from using a CAR from the 6 channels in the 6-channel configuration of the present invention.
Figure 10B:
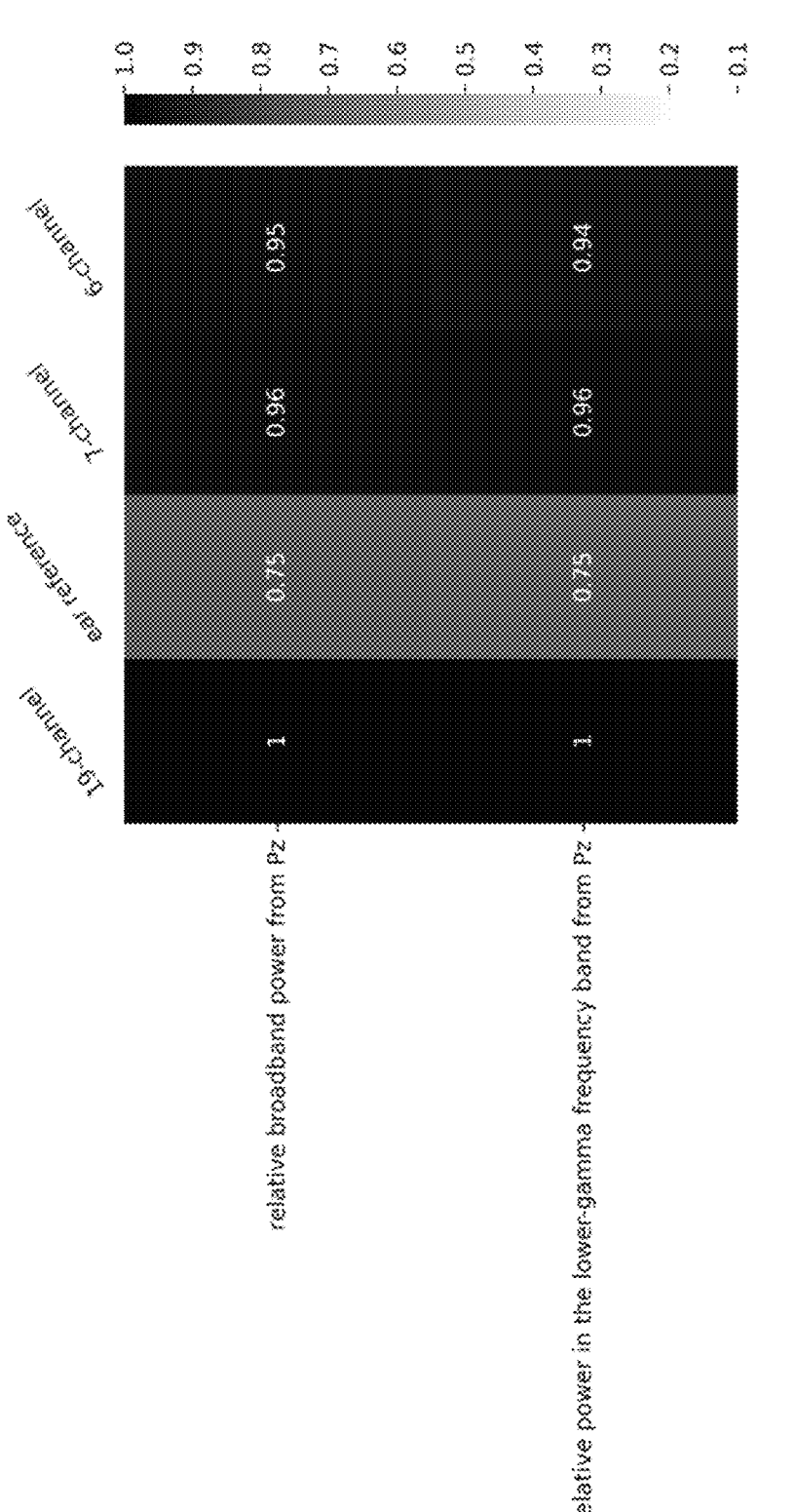
FIG. 10B is a table showing, for the test set of data, the correlation between relative power of the signal from the Pz electrode when re-referenced with a CAR using all 19 channels from a subset of the 10-10 system to when it was re-referenced in various ways. The value shown in the table is the spearman correlation coefficient. By row, either the relative broadband power (top) or the relative power in the lower-gamma frequency band (bottom) from Pz using a 19-channel CAR is compared to (by column) itself, the value from the original ear-referenced signal without using any CAR, the value from using a CAR from the 7 channels in the 7-channel configuration of the present invention, and the value from using a CAR from the 6 channels in the 6-channel configuration of the present invention.

On the test set of data (the remaining 50% of the agomelatine data, age and gender balanced), the 7-channel configuration (F7-Fz-F8-Cz-P7-Pz-P8) and the 6-channel configuration (Cz-Pz-Fp1-Fp2-P7-P8) passed all of the above criteria set before testing for consistency with the current biomarker, clinical relevance, and reliability of the biomarker feature on the Pz electrode. The ear-referenced signal did not pass. This is shown in FIGS. 7-10B. FIGS. 7, 8A-8C, 9A-9B, and 10A-10B are charts showing metrics for replication of the current biomarker (sample entropy in the lower gamma range) that is predictive of effective agomelatine treatment in a patient using the test set of data for each electrode configuration and an ear reference. The chart of FIG. 7 shows that the sample entropy measures from the 7- and 6-channel configurations are well correlated (having values above 0.80) with those from the full set of electrodes (CAR). In contrast, the ear reference was not correlated with the sample entropy CAR measurement. The charts of FIGS. 8A, 8B, and 8C show a comparison between the biomarker status determined from the re-referenced signal (either Positive or Negative) and the current biomarker (shown as "biomarker_original") for the 7-channel and 6-channel, and ear-referenced configurations, respectively. Based on the data in FIGS. 8A-8C, one can calculate the "sensitivity" (that is, out of all the people that have the biomarker, what percent were positive for the EEG measurement), which preferably is at least 85%; and percentage of "precision" (that is, out of all predicted as positive, what percent are really positive), which preferably is above 85%. The 7-channel configuration showed sensitivity above 85% (with a sensitivity of 89%), but the 6-channel and ear-referenced data did not (with sensitivity of 81% and 59% respectively). The 7-channel configuration also showed precision above 85% (with a precision of 92%), while the 6-channel and ear-referenced data did not (with precision of 81% and 59% respectively). One can also calculate the fraction of the population whose biomarker status should have been negative but is now positive which preferably is at most 10%; both the 7-channel configuration and the 6-channel configuration met this criterion (3.8% and 9.3%, respectively), but the ear-reference did not (20.4%). One can also calculate the fraction of the population whose biomarker status should have been positive but is now negative which preferably is at most 10%; both the 7-channel configuration and the 6-channel configuration met this criterion (5.8% and 9.3%, respectively), but the ear-reference did not (20.4%). FIG. 9A shows the correlation between the sample entropy biomarker to the percent change in MADRS from baseline to week 6 (top row) and to the absolute change in MADRS from baseline to week 6 (bottom row); the correlation for sample entropy measured with the reduced electrode measurements was within a tolerance of 0.05. FIG. 9B shows the biomarker feature reliability from the Pz electrode using the reduced electrode measurements within 0.2 of the reliability of the CAR. The charts of FIGS. 10A and 10B show that the spectral features and power from the CAR and each of the 7-channel and 6-channel electrode configurations are well correlated (i.e., Spearman correlation values of 0.85 or higher).

FIGS. 11-14B show for the entire agomelatine study dataset (the training and test sets combined) the comparison between the data when using the 19-channel CAR and the data when using a reduced electrode configuration CAR (e.g., the aforementioned 7-channel or 6-channel configuration). Table 2 below shows the criteria for the comparison between the 19-channel CAR configuration and the full set of data for each reduced electrode configuration (7-channel and 6-channel) as well as the ear reference.

TABLE 2

| Re-referencing Scheme | 7-channel (F7-FZ-F8-CZ-P7-PZ-P8) | 6-channel (CZ-PZ-FP1-FP2-P7-P8) | Ear-reference |
|---|---|---|---|
| Consistency with Current Biomarker | | | |

TABLE 2-continued

| Re-referencing Scheme | 7-channel (F7-FZ-F8-CZ-P7-PZ-P8) | 6-channel (CZ-PZ-FP1-FP2-P7-P8) | Ear-reference |
|---|---|---|---|
| (should meet 3 of 5) | | | |
| Correlation with current biomarker feature value above 0.80 | ✓ | ✓ | X |
| Precision (out of all predicted as positive, how many are really positive?) above 85% | ✓ | X | X |
| Sensitivity (out of all the people that have the biomarker, how many got positive results?) above 85% | ✓ | X | X |
| The percent of the population whose biomarker status should have been negative but is now positive should be at most 10% | ✓ | ✓ | X |
| The percent of the population whose biomarker status should have been positive but is now negative should be at most 10% | ✓ | ✓ | X |
| Clinical relevance: | | | |
| Correlation with percent change in MADRS from baseline to week 6 equal to or greater than the correlation the CAR biomarker had, with a 0.05 tolerance | ✓ | ✓ | ✓ |
| Correlation with absolute change in MADRS from baseline to week 6 equal to or greater than the correlation the CAR biomarker had, with a 0.05 tolerance | ✓ | ✓ | ✓ |
| Feature reliability from PZ electrode: | | | |
| CCC within 0.2 of the reliability of the CAR biomarker | ✓ | ✓ | X |

Figure 11:
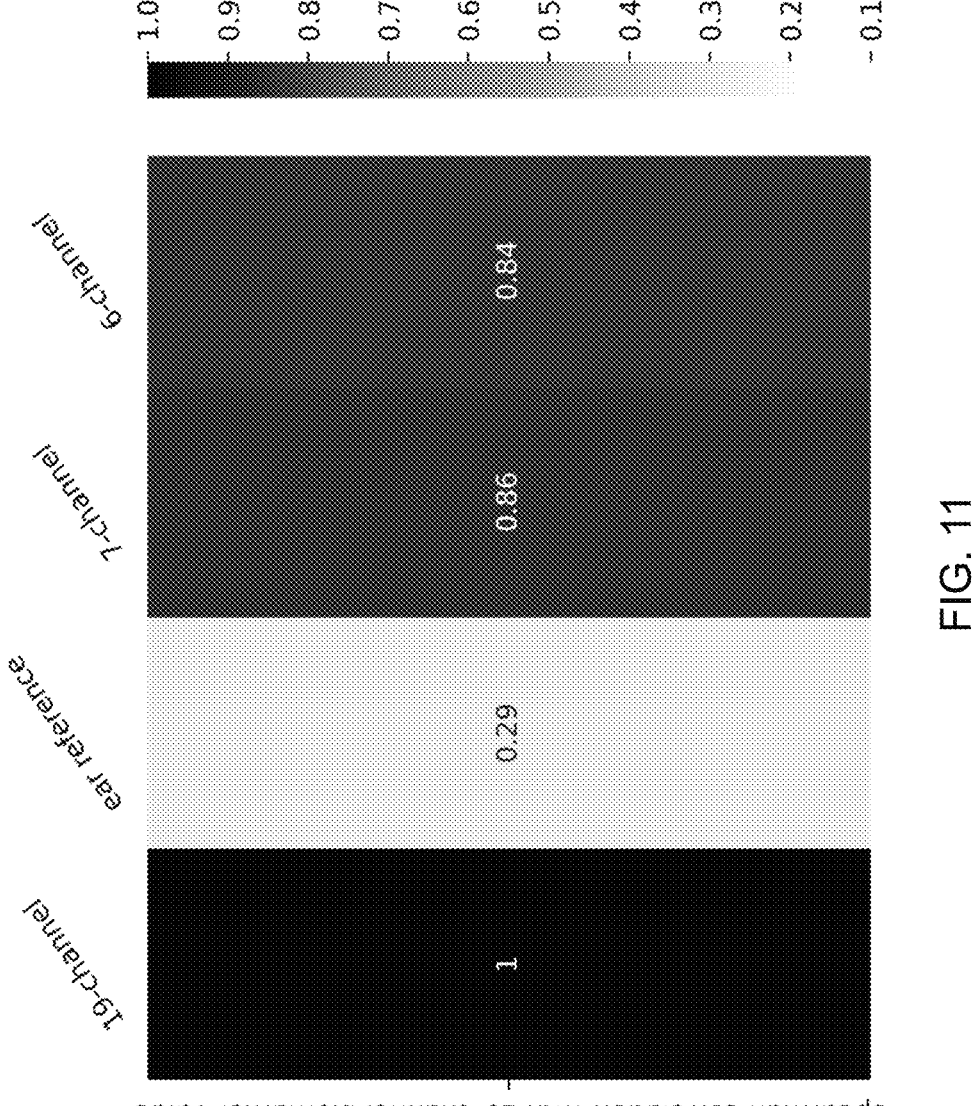
FIG. 11 is a table comparing, on the complete set of data, the value of sample entropy in the low-gamma (30-40 Hz) band from the Pz electrode when re-referenced with a common average reference (CAR) using all 19 channels from a subset of the 10-10 system (referred to as the 19-channel biomarker value in the row label) to the value of sample entropy in the low-gamma band from the Pz electrode when referenced in a variety of ways. The value shown in each cell of the table is the spearman correlation coefficient. The biomarker when referenced using a 19-channel CAR is compared to (by column) itself, the original ear-referenced signal without using any CAR, the signal when using a CAR from the 7 channels in the 7-channel configuration of the present invention, and the signal when using a CAR from the 6 channels in the 6-channel configuration of the present invention.
Figure 12B:
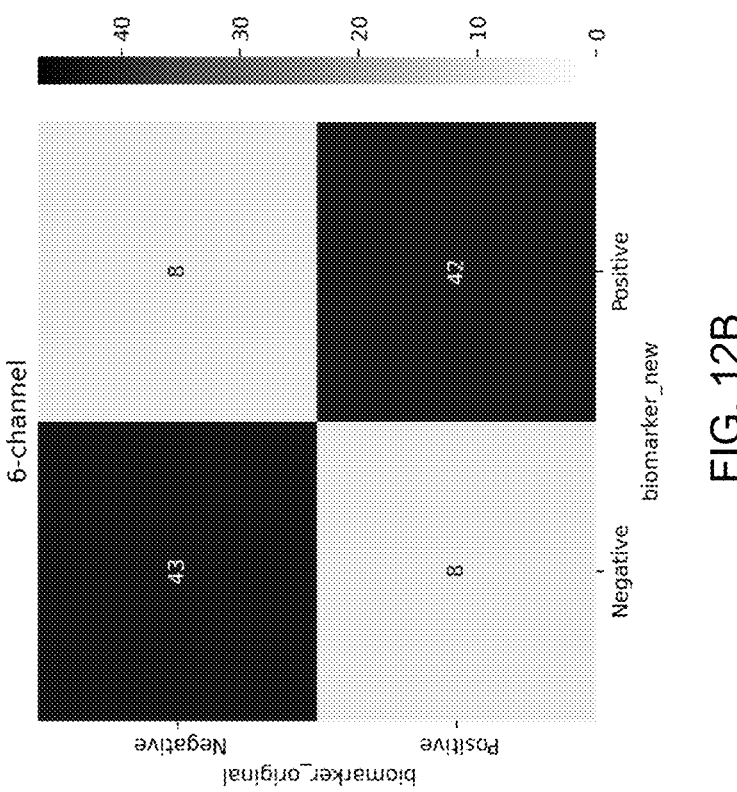
FIG. 12A-C contains confusion matrices, from the complete set of data, comparing biomarker status (either Positive or Negative) from when the biomarker was calculated using a 19-channel CAR (y-axis, "biomarker_original") to when the biomarker was calculated using (12A) a CAR from the 7 channels in the 7-channel configuration of the present invention, (12B) a CAR from the 6 channels in the 6-channel configuration of the present invention, or (12C) the original ear-referenced signal without any CAR (x-axis, "biomarker_new").
Figure 12A:
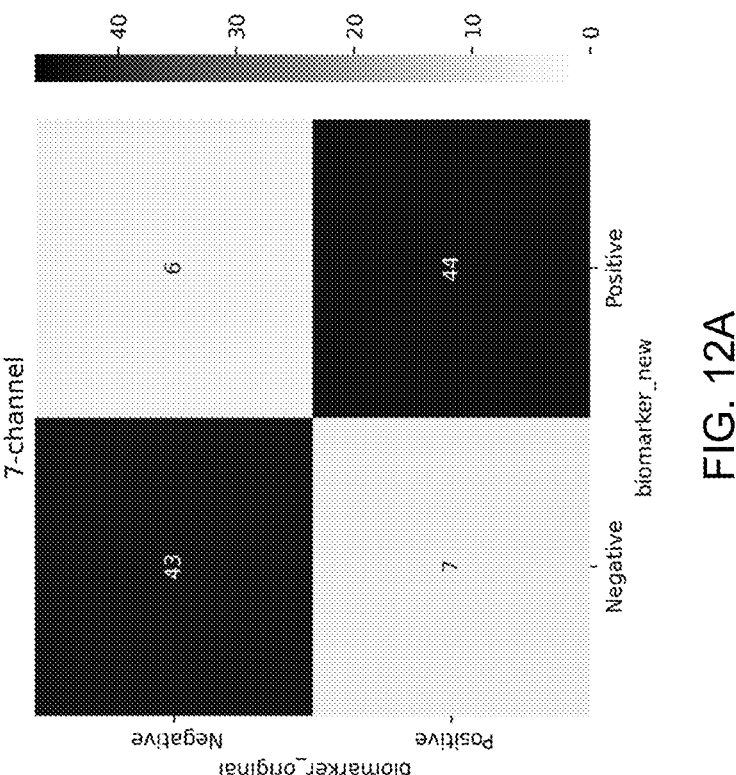
Figure 12C:
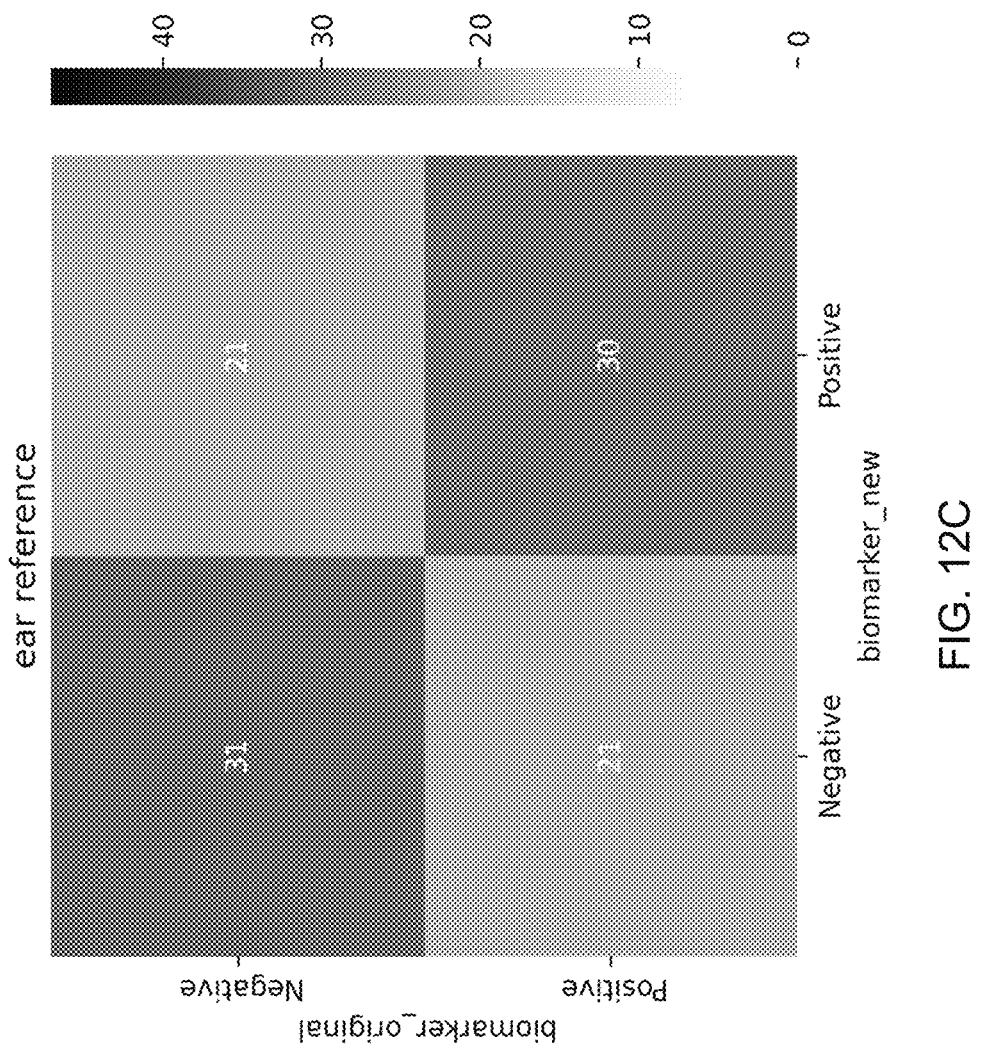
Figure 13A:
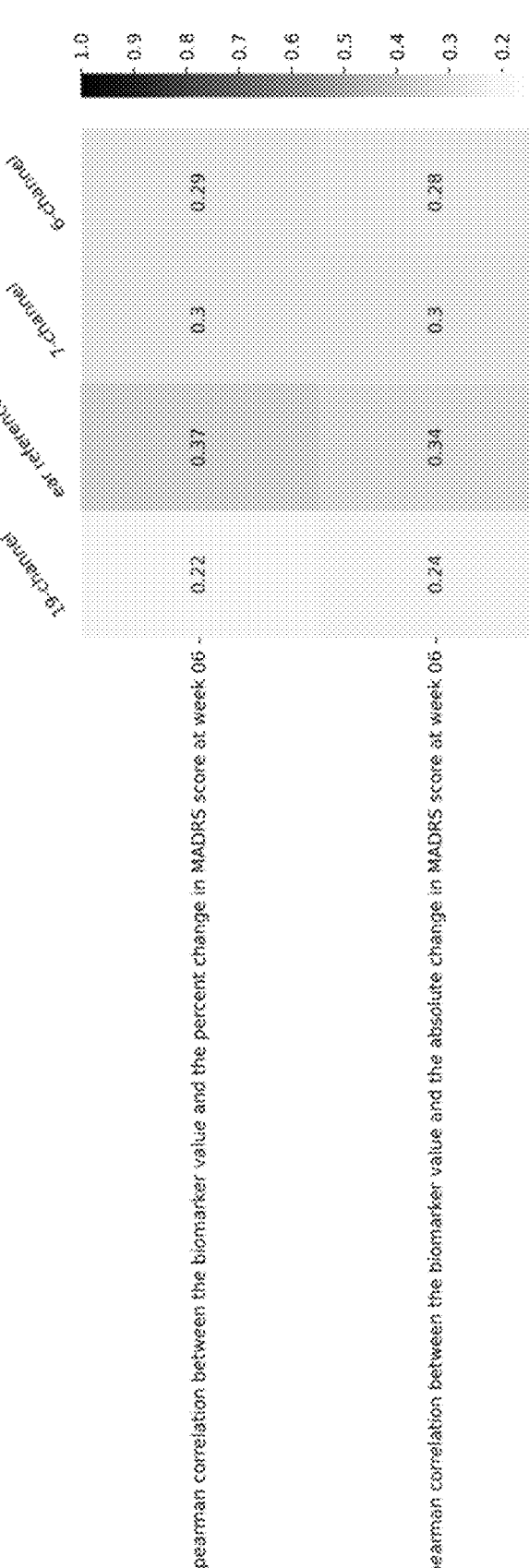
FIG. 13A is a table showing, for the complete set of data, the correlation between the biomarker value and either the percent change in the Montgomery-Åsberg Depression Rating Scale (MADRS) between baseline and week 6 (top row) or the absolute change in the MADRS between baseline and week 6 (bottom row). Each column shows the spearman correlation coefficient when the biomarker value (sample entropy in the low-gamma band from the Pz electrode) is re-referenced in a different way (by column): using a 19-channel CAR, using the original ear-referenced signal without using any CAR, using the signal when using a CAR from the 7 channels in the 7-channel configuration of the present invention, and using the signal when using a CAR from the 6 channels in the 6-channel configuration of the present invention.
Figure 13B:
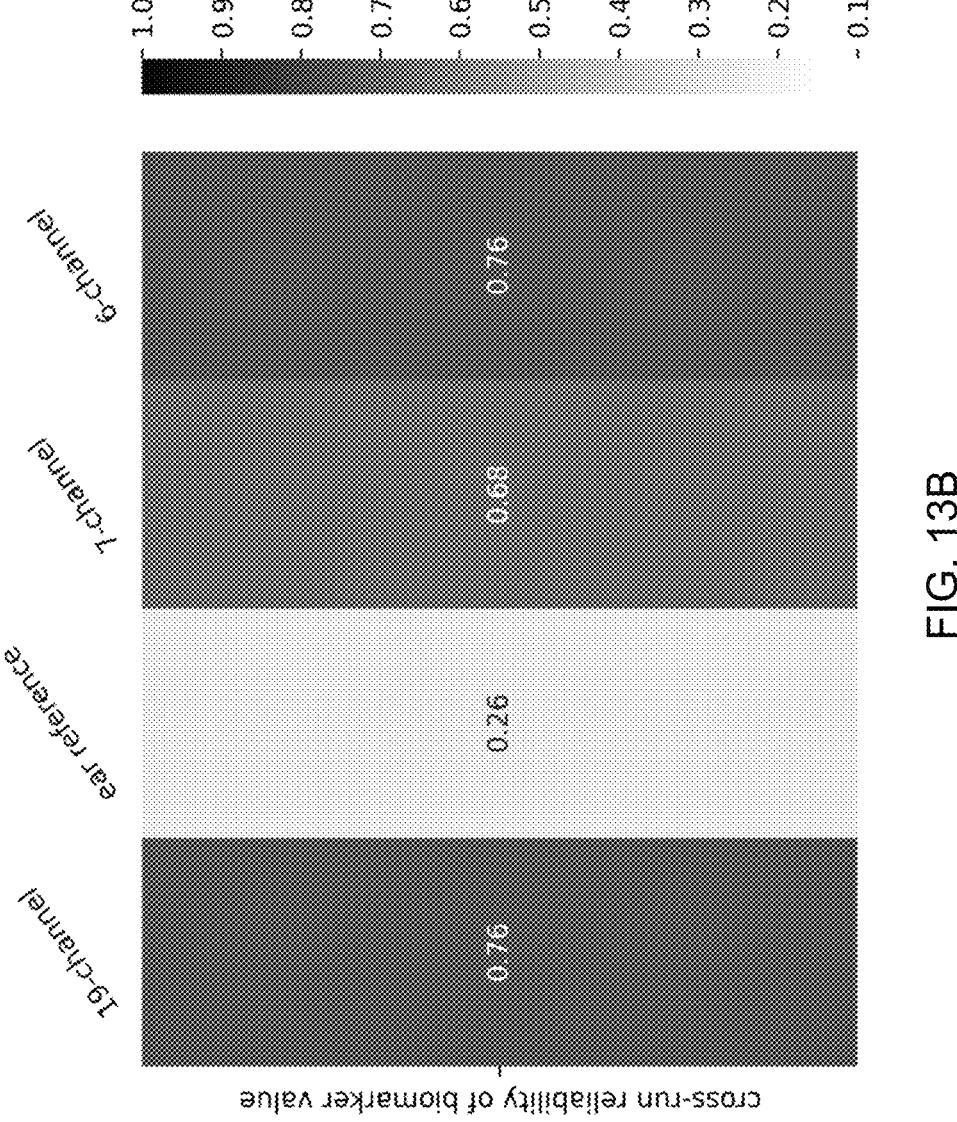
FIG. 13B is a table showing, for the complete set of data, the reliability of the biomarker value when calculated on two separate 4-minute resting eyes closed (REC) recordings. Each column shows the concordance correlation coefficient between the value from the two recordings when the biomarker value of sample entropy in the low-gamma band from the Pz electrode is re-referenced in different ways (by column): using a 19-channel CAR, using the original ear-referenced signal without using any CAR, using the signal when using a CAR from the 7 channels in the 7-channel configuration of the present invention, and using the signal when using a CAR from the 6 channels in the 6-channel configuration of the present invention.
Figure 14A:
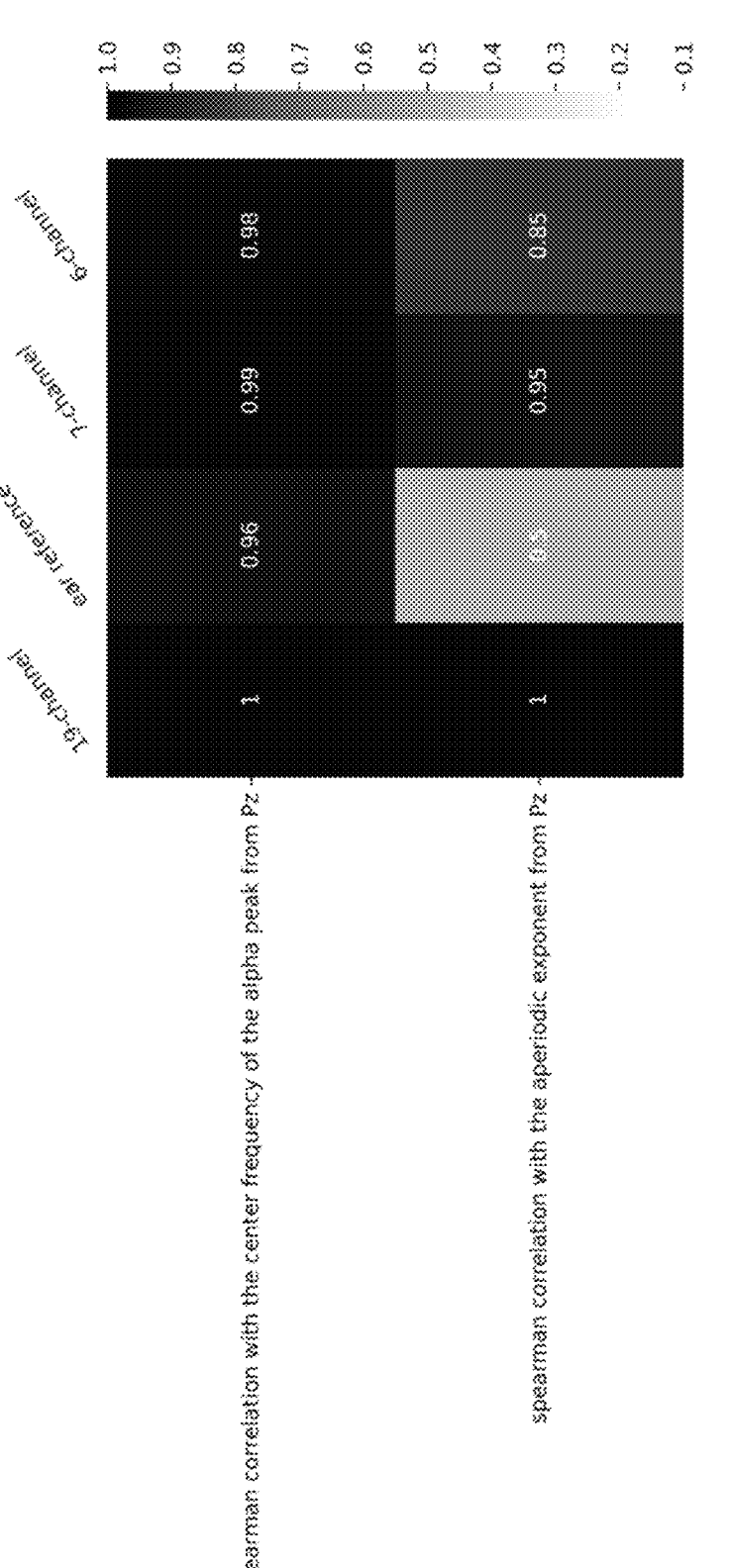
FIG. 14A is a table showing, for the complete set of data, the correlation between spectral features of the signal from the Pz electrode when re-referenced with a CAR using all 19 channels from a subset of the 10-10 system to when it was re-referenced in various ways. The value shown in each cell of the table is the spearman correlation coefficient. By row, either the center frequency of the alpha peak (top) or the aperiodic exponent (bottom) from Pz using a 19-channel CAR is compared to (by column) itself, the value from the original ear-referenced signal without using any CAR, the value from using a CAR from the 7 channels in the 7-channel configuration of the present invention, and the value from using a CAR from the 6 channels in the 6-channel configuration of the present invention.
Figure 14B:
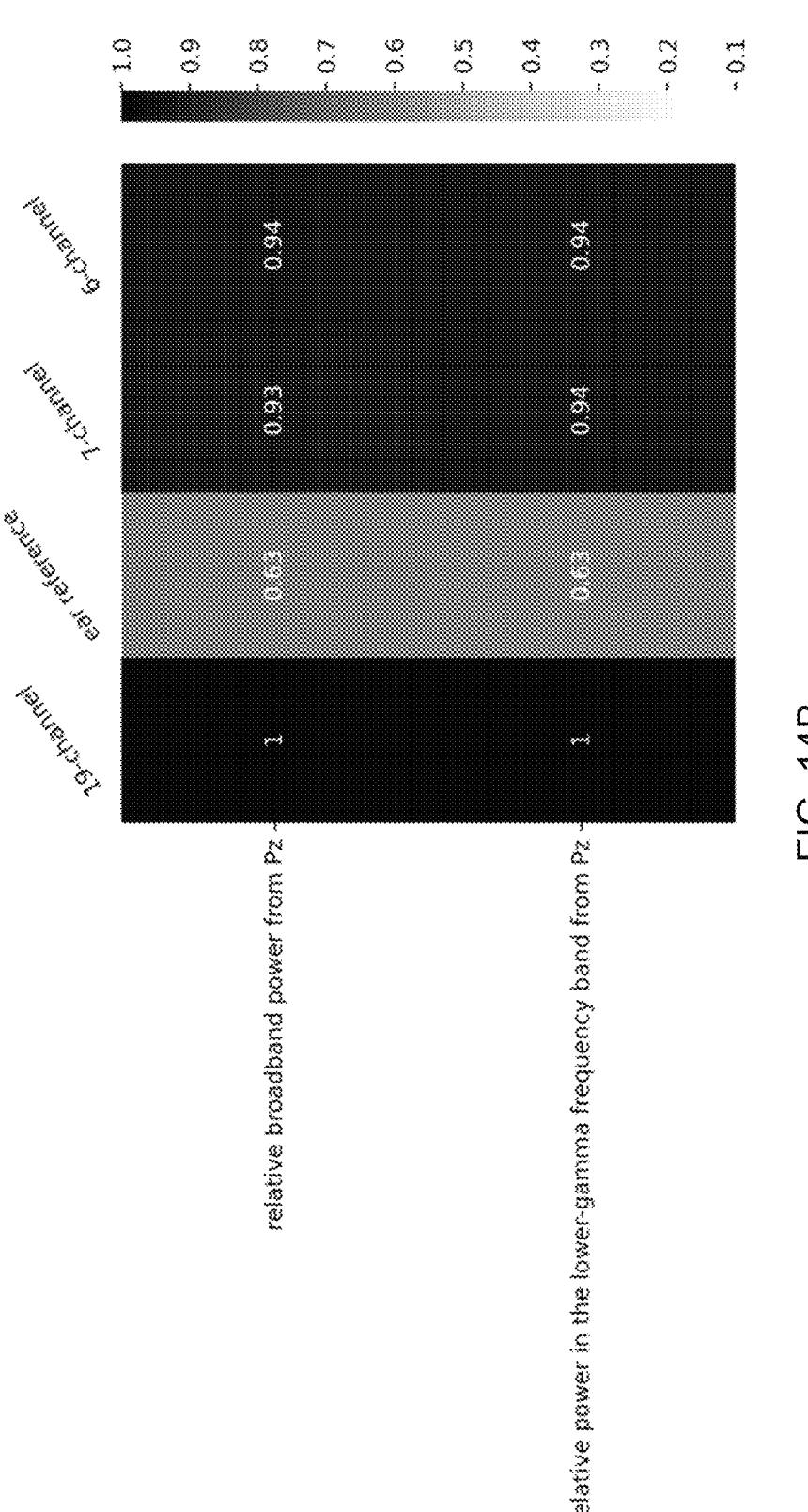
FIG. 14B is a table showing, for the complete set of data, the correlation between relative power of the signal from the Pz electrode when re-referenced with a CAR using all 19 channels from a subset of the 10-10 system to when it was re-referenced in a variety of ways. The value shown in each cell of the table is the spearman correlation coefficient. By row, either the relative broadband power (top) or the relative power in the lower-gamma frequency band (bottom) from Pz using a 19-channel CAR is compared to (by column) itself, the value from the original ear-referenced signal without using any CAR, the value from using a CAR from the 7 channels in the 7-channel configuration of the present invention, and the value from using a CAR from the 6 channels in the 6-channel configuration of the present invention.

For the entire dataset for the agomelatine trial, the 7-channel and the 6-channel configurations passed the required qualifications. This is shown in FIGS. 11-14B. FIGS. 11, 12A-12C, and 13A-13B are charts showing metrics for replication of the current biomarker (sample entropy in the lower gamma range from the Pz electrode after CAR re-referencing) that is predictive of effective treatment in a patient using the entire set of data for each electrode configuration and the ear reference. The chart of FIG. 11 is similar to FIG. 7 showing the correlation with the current biomarker feature value above 0.80, except FIG. 11 relates to the entire set of data, whereas FIG. 7 relates to only the test set. The charts of FIGS. 12A, 12B, and 12C compare biomarker status (Positive or Negative) with the current biomarker (shown as "biomarker_original") for each of the 7-channel, 6-channel, and ear-referenced configurations, respectively, similar to FIGS. 8A, 8B, and 8C, respectively, but for the full set of data. Like FIGS. 8A-8C, FIGS. 12A-12C show acceptable sensitivity and precision for the 7-channel electrode configuration (sensitivity of 86% and precision of 88%) but not the 6-channel configuration (sensitivity of 84% and precision of 84%) or the ear-reference (sensitivity of 59% and precision of 59%). The fraction of the population whose biomarker status should have been negative but is now positive met criteria (<10%) for the 7-channel configuration (6%) and the 6-channel configuration (7.9%) but not the ear-reference (20.4%). The fraction of the population whose biomarker status should have been positive but is now negative also met criteria (<10%) for the 7-channel configuration (7%) and the 6-channel configuration (7.9%) but not the ear-reference (20.4%). The charts of FIGS. 13A and 13B are similar to those in FIGS. 9A and 9B but for the entire set of data, rather than just the test set, and similarly shows the correlation for sample entropy measured with the reduced electrode measurements was within a tolerance of 0.05 (compared to the CAR measurement). The charts of FIGS. 14A and 14B are similar to those of FIGS. 10A and 10B, except they relate to the full set of collected data; they similarly show that the spectral features and power from the CAR and each of the 7-channel and 6-channel electrode configurations are well correlated.

The 7-channel configuration (F7-Fz-F8-Cz-P7-Pz-P8) passed the criteria for a successfully replicated signal on both the test data and the entire dataset from the agomelatine study. The 7-channel electrode configuration provides a significant reduction in the number of channels, thereby reducing complexity of the application. While only the 7 channels (F7-Fz-F8-Cz-P7-Pz-P8) would be used for the CAR re-referencing of the Pz electrode in biomarker calculation, 8-channel configurations including one additional channel would improve either the ability to characterize alpha (in the case of embodiment (ii) F7-Fz-F8-Cz-P7-Pz-P8-Oz, where the Oz channel is used for alpha characterization) or the ability to detect and reject artifacts (in the case of embodiments (iii) F7-Fz-F8-Cz-P7-Pz-P8-Fpz and (iv) F7-Fz-F8-Cz-P7-Pz-P8-AUX, where the Fpz or auxiliary channel respectively would be used for artifact handling).

It will be apparent to those skilled in the art having the benefit of the teachings presented in the foregoing descriptions and the associated drawings that modifications, combinations, sub-combinations, and variations can be made without departing from the spirit or scope of this disclosure. Likewise, the various examples described may be used individually or in combination with other examples. Those skilled in the art will appreciate various combinations of examples not specifically described or illustrated herein that are still within the scope of this disclosure. In this respect, it is to be understood that the disclosure is not limited to the specific examples set forth and the examples of the disclosure are intended to be illustrative, not limiting.

As used in this specification and the appended claims, the singular forms "a", "an" and "the" include plural referents, unless the context clearly dictates otherwise. Similarly, the adjective "another," when used to introduce an element, is intended to mean one or more elements. The terms "comprising," "including," "having" and similar terms are intended to be inclusive such that there may be additional elements other than the listed elements.

Additionally, the methods described above or the method claims below do not explicitly require an order to be followed by its steps or an order is otherwise not required based on the description or claim language, it is not intended that any particular order be inferred. Likewise, where a method claim below does not explicitly recite a step mentioned in the description above, it should not be assumed that the step is required by the claim.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A method of selecting a patient suffering from depression for an agomelatine treatment and treating the patient, the method comprising:

collecting brain wave activity data via a configuration of EEG electrodes applied to the patient, wherein the configuration is a 7-channel electrode configuration consisting of EEG electrodes at: F7-Fz-F8-Cz-P7-Pz-P8, according to the 10-10 system of electrode placement;

analyzing the brain wave activity data to calculate one or more EEG measures, wherein at least one of the one or more EEG measures are selected from a group consisting of: an EEG measure of entropy, an EEG measure of complexity, or any combination thereof;

predicting an outcome of the agomelatine treatment in the patient based on the one or more EEG measures;

selecting the patient for agomelatine treatment based on the outcome prediction; and when the patient is selected for agomelatine treatment based on the one or more EEG measures, administering an effective amount of agomelatine, a prodrug thereof, or a pharmaceutically acceptable salt thereof to treat the depression of the patient.

2. The method of claim 1, wherein at least one of the one or more EEG measures comprises EEG sample entropy.

3. The method of claim 1, wherein at least one of the one or more EEG measures comprises EEG sample entropy at the Pz electrode.

4. The method of claim 3, wherein a signal from the Pz electrode is re-referenced using a common average reference from the 7 EEG electrodes in the 7-channel configuration, and wherein the sample entropy is calculated after the signal from the Pz electrode is re-referenced.

5. The method of claim 1, wherein at least one of the one or more EEG measures are selected from a group consisting of: measures of predictability, measures of regularity, or any combination thereof.

6. The method of claim 1, wherein at least one of the one or more EEG measures are selected from a group consisting of: approximate entropy, detrended fluctuation analysis, Higuchi fractal dimension, Katz fractal dimension, largest Lyapunov exponent, modified multiscale entropy, multiscale entropy, aperiodic exponent, or any combination thereof.

7. The method of claim 1, wherein the one or more EEG measures are analyzed with stored historical subject data containing data from a plurality of subjects having a depressive disorder, who received treatment with agomelatine, a prodrug thereof, or a pharmaceutically acceptable salt thereof, and wherein the stored historical subject data includes, for the plurality of the subjects, the efficacy of the agomelatine treatment and one or more of the same type of EEG measures as calculated for the patient.

8. The method of claim 7, wherein the step of predicting an outcome of the agomelatine treatment in the patient comprises determining an agomelatine efficacy likelihood score for the patient based on the stored historical subject data, and wherein the step of selecting the patient for agomelatine treatment based on the outcome prediction comprises selecting the patient based on the likelihood score.

* * * * *